(12) United States Patent
Lewandowski et al.

(10) Patent No.: US 10,941,234 B2
(45) Date of Patent: Mar. 9, 2021

(54) KETONE-CONTAINING CONTROLLED RADICAL INITIATORS FOR POLYMERIZATION REACTIONS

(71) Applicant: 3M INNOVATIVE PROPERTIES COMPANY, St. Paul, MN (US)

(72) Inventors: Kevin M. Lewandowski, Inver Grove Heights, MN (US); Stephen B. Roscoe, Woodbury, MN (US); Babu N. Gaddam, Woodbury, MN (US); Bryan T. Whiting, St. Paul, MN (US); John L. Battiste, Northfield, MN (US); George W. Griesgraber, Eagan, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 15/733,412

(22) PCT Filed: Feb. 13, 2019

(86) PCT No.: PCT/IB2019/051165
§ 371 (c)(1),
(2) Date: Jul. 23, 2020

(87) PCT Pub. No.: WO2019/162805
PCT Pub. Date: Aug. 29, 2019

(65) Prior Publication Data
US 2020/0369820 A1    Nov. 26, 2020

Related U.S. Application Data

(60) Provisional application No. 62/633,337, filed on Feb. 21, 2018.

(51) Int. Cl.
*C08F 293/00* (2006.01)
*C08F 265/06* (2006.01)
(Continued)

(52) U.S. Cl.
CPC ........ *C08F 293/005* (2013.01); *C07C 329/16* (2013.01); *C07C 333/20* (2013.01);
(Continued)

(58) Field of Classification Search
CPC .......... C08F 2/38; C08F 2/48; C08F 293/005; C08F 265/06; C08F 2438/03;
(Continued)

(56) References Cited

U.S. PATENT DOCUMENTS 2,716,633 A    8/1955    Engelhardt
4,181,752 A    1/1980    Martens
(Continued)

FOREIGN PATENT DOCUMENTS

DE    840239    5/1952
EP    0286376    10/1988
(Continued)

OTHER PUBLICATIONS

Machine-generated English-language translation of JP-2006045387-A.*

(Continued)

*Primary Examiner* — Vu A Nguyen
(74) *Attorney, Agent, or Firm* — Jean A. Lown

(57) ABSTRACT

Controlled radical initiators that are ketone-containing dithiocarbamate or ketone-containing dithiocarbonate compounds are used to form polymeric materials that have a single polymeric block or multiple polymeric blocks. Reaction mixtures containing controlled radical initiators and various ethylenically unsaturated monomers, polymeric materials formed from the reaction mixtures, crosslinkable compositions containing the polymeric materials, crosslinked compositions formed from the crosslinkable compo-
(Continued)

sitions, and articles containing the polymeric materials, the crosslinkable compositions, or the crosslinked compositions are provided.

15 Claims, 2 Drawing Sheets

(51) Int. Cl.

| | |
|---|---|
| C07C 329/16 | (2006.01) |
| C07C 333/20 | (2006.01) |
| C09J 4/06 | (2006.01) |
| C09J 153/00 | (2006.01) |
| C09J 133/08 | (2006.01) |

(52) U.S. Cl.
CPC .............. *C08F 265/06* (2013.01); *C09J 4/06* (2013.01); *C09J 133/08* (2013.01); *C09J 153/00* (2013.01); *C08F 2438/03* (2013.01)

(58) Field of Classification Search
CPC ........ C07C 329/16; C07C 330/20; C09J 4/06; C09J 133/08; C09J 153/00
See application file for complete search history.

(56) References Cited

U.S. PATENT DOCUMENTS

| | | | |
|---|---|---|---|
| 4,329,384 A | 5/1982 | Vesley | |
| 4,330,590 A | 5/1982 | Vesley | |
| 4,379,201 A | 4/1983 | Heilmann | |
| 5,506,279 A | 4/1996 | Babu | |
| 5,773,485 A | 6/1998 | Bennett | |
| 6,153,705 A | 11/2000 | Corpart | |
| 2003/0191262 A1* | 10/2003 | McCormick | C07C 327/36 526/288 |
| 2011/0046324 A1* | 2/2011 | Matyjaszewski | C08F 293/005 526/90 |
| 2013/0165606 A1 | 6/2013 | Prenzel | |
| 2014/0288242 A1 | 9/2014 | Prenzel | |
| 2014/0329971 A1 | 11/2014 | Prenzel | |

FOREIGN PATENT DOCUMENTS

| | | | |
|---|---|---|---|
| EP | 0349270 | | 1/1990 |
| JP | 1030078 | | 2/1998 |
| JP | 2006045387 A | * | 2/2006 |
| WO | WO 2009-090253 | | 7/2009 |
| WO | WO 2018-013330 | | 1/2018 |
| WO | WO 2018-118905 | | 6/2018 |
| WO | WO 2018-177989 | | 10/2018 |
| WO | WO 2018-178829 | | 10/2018 |
| WO | WO 2019-162806 | | 8/2019 |

OTHER PUBLICATIONS

SciFinder Search (Oct. 23, 2020).*
Anthore-Dalion, "A Radical Bidirectional Fragment Coupling Route to Unsymmetrical Ketones", Journal of the American Chemical Society, Jun. 2016, vol. 138, pp. 8404-8407.
Azizi, "An efficient four-component synthesis of dithiocarbamate derivatives", Tetrahedron Letters, 2013, vol. 54, pp. 5407-5410, XP28696453.
Bak, Synthese stabiler a-Oxo-methylen-bis-ethylxanthogenate, 1979, vol. 103, No. 11, pp. 363-365.
Bhattacharya, "A General Synthesis of 1,3-Dithiol-2-ones", Journal of Organic Chemistry, Jan. 1974, vol. 39, No. 1, pp. 95-97.
Briggs, "A new approach to the synthesis of polycyclic structures", Tetrahedron Letters, 2004, vol. 45, pp. 6017-6020.
Brown, "A New General Synthesis of 2- (N-Mono- and N-Di-substituted Amino) thiazoles", Journal of the Chemical Society, Perkin Transactions 1, 1985, pp. 1623-1626.
Destarac, "Macromolecular Design via the Interchange of Xanthates (MADIX): Polymerization of Styrene with O-Ethyl Xanthates as Controlling Agents", Macromolecular Chemistry and Physics, 2002, vol. 203, No. 16, pp. 2281-2289.
Destarac, "Madix Technology: From Innovative Concepts to Industrialization", Polymer Preprints, 2008, vol. 49, No. 2, pp. 179-180.
Heng, "Substitution of chlorocyclobutanones with xanthate salts. The remarkable effect of added base", Tetrahedron Letters, 2009, vol. 50, pp. 3613-3616.
Holsboer, "Synthesis of O-Methyl Thioformate", Recueil, 1972, vol. 91, No. 11, pp. 1371-1372.
Kuriyama, "Living Radical Polymerization of Methyl Methacrylate with a Tetrafunctional Photoiniferter: Synthesis of a Star Polymer", Polymer Journal, 1984, vol. 16, No. 6, pp. 511-514.
Mattioni, "Prediction of glass transition temperatures from monomer and repeat unit structure using computational neural networks", Journal of Chemical Information and Computer Sciences, Mar.-Apr. 2002, vol. 42, No. 2, pp. 232-240.
Otsu, "Living Mono- and Biradical Polymerizations in Homogeneous System Synthesis of AB and ABA Type Block Copolymers", Polymer Bulletin, 1984, vol. 11, pp. 135-142.
Otsu, "Role of initiator-transfer agent-terminator (iniferter) in radical polymerizations: Polymer design by organic disulfides as iniferters", Feb. 1982, vol. 3, pp. 127-132.
Poladura, "TBD-catalyzed a-sulfenylation of cyclic ketones: desymmetrization of 4-substituted cyclohexanones", Tetrahedron, 2012, vol. 68, pp. 6438-6446.
Quiclet-Sire, "A direct, versatile route to functionalized trialkoxysilanes", Chemical Communication, Jan. 2014, vol. 50, No. 18, pp. 2324-2326.
Tasdelen, "A New Photoiniferter/RAFT Agent for Ambient Temperature Rapid and Well-Controlled Radical Polymerization", Journal of Polymer Science Part A Polymer Chemistry, 2008, vol. 46, pp. 3387-3395, XP2555987.
Taton, Handbook of Raft Polymerization, (373), 2008.
Tsarevsky, "Controlled Radical Polymerization: Mechanisms", ACS Symposium Series, American Chemical Society, 2015, pp. 211-246.
Veetil, "Photochemistry of S-Phenacyl Xanthates", the Journal of Organic Chemistry, 2011, vol. 76, pp. 8232-8242, XP55322858.
International Search Report for PCT International Application No. PCT/IB2019/051165, dated Jun. 6, 2019, 5 pages.

* cited by examiner

KETONE-CONTAINING CONTROLLED RADICAL INITIATORS FOR POLYMERIZATION REACTIONS

CROSS REFERENCE TO RELATED APPLICATION

This application is a national stage filing under 35 U.S.C. 371 of PCT/IB2019/051165, filed Feb. 13, 2019, which claims the benefit of U.S. Provisional Patent Application No. 62/633,337, filed Feb. 21, 2018, the disclosure of which is incorporated by reference herein in its entirety.

TECHNICAL FIELD

Polymeric materials and reaction mixtures used to form the polymeric materials are provided; the reaction mixtures contain a controlled radical initiator that is a ketone-containing dithiocarbamate or dithiocarbonate compound.

BACKGROUND

The performance characteristics of polymeric materials are determined not only by their composition but also by their molecular architecture. For copolymers, various properties such as melt viscosity, glass transition temperature, and modulus are often a function of the distribution of the different monomeric units along the polymeric chain. Conventional radical polymerization methods have limited utility in synthesizing polymers with precise architectural and structural characteristics.

Controlled radical polymerization methods have been developed that allow the preparation of polymers with well-defined molecular weight, polydispersity, topology, composition, and microstructure. These methods are based on the use of special polymerization mediators, which temporarily and reversibly transform propagating radicals into dormant and/or stable species. These reversible transformations are typically either accomplished by reversible deactivation or by reversible chain transfer. Some of the methods that involve controlled radical polymerization through reversible transformations include iniferter methods, nitroxide mediated polymerization (NMP) methods, atom transfer polymerization (ATRP) methods, and reversible addition-fragmentation (RAFT) methods.

The terms "iniferter" and "photoiniferters" refer to molecules that can act as an initiator, chain transfer agent, and terminator. Various iniferters were discussed in Otsu et al., *Makromol. Chem., Rapid Commun.*, 3, 127-132 (1982). The compound p-xylene bis(N,N-diethyldithiocarbamate) (XDC) has been used to form various acrylic-based block copolymers such as those described in European Patent Applications 0286376 A2 (Otsu et al.) and 0349270 A2 (Mahfuza et al.).

Some polymeric materials have been formed by applying a layer of a crosslinkable composition to the surface of a substrate. The crosslinkable composition can contain a prepolymer, additional monomers, and a crosslinking agent. Crosslinked compositions can be prepared by exposing the crosslinkable composition to actinic radiation such as ultraviolet radiation. Such polymeric materials and processes are described in U.S. Pat. Nos. 4,181,752 (Martens et al.), 4,330,590 (Vesley), 4,329,384 (Vesley et al.), 4,379,201 (Heilmann et al.), 5,506,279 (Babu et al.), 5,773,836 (Bennett et al.), and 5,773,485 (Bennett et al.).

SUMMARY

Reaction mixtures containing controlled radical initiators and various ethylenically unsaturated monomers are provided. Additionally, polymeric materials formed from the reaction mixtures, crosslinkable compositions containing the polymeric materials, crosslinked compositions formed from the crosslinkable compositions, and articles containing the polymeric materials, the crosslinkable compositions, or the crosslinked compositions are provided. The controlled radical initiators are ketone-containing dithiocarbamate or ketone-containing dithiocarbonate compounds.

In a first aspect, a polymeric material of Formula (II) is provided.

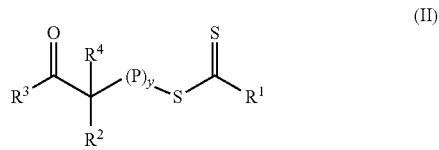

(II)

In Formula (II), group $R^1$ is an alkoxy, aralkyloxy, alkenoxy or $-N(R^5)_2$. Group $R^2$ and $R^3$ are each independently an alkyl, aryl, aralkyl, alkaryl, or a group of formula $-R^6-(OR^6)_n-OR^7$, or $R^2$ and $R^3$ combine to form a ring structure containing the carbonyl group. Group $R^4$ is hydrogen or alkyl. Each $R^5$ is an alkyl, aryl, or two adjacent $R^5$ groups combine with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. Each P is a polymeric block that comprises a polymerized product of a first monomer composition comprising at least one first monomer having a single ethylenically unsaturated group and y is an integer in a range of 1 to 10.

In a second aspect, a first reaction mixture is provided. The reaction mixture contains a) a photoinitiator of Formula (I)

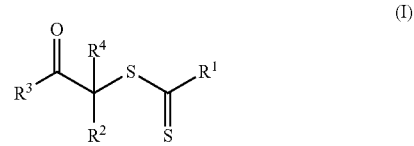

(I)

and b) a first monomer composition comprising at least one first monomer having a single ethylenically unsaturated group, wherein a molar ratio of monomers (e.g., ethylenically unsaturated groups) in the first monomer composition to the photoinitiator is at least 3:1. In Formula (I), group $R^1$ is an alkoxy, aralkyloxy, alkenoxy or $-N(R^5)_2$. Group $R^2$ and $R^3$ are each independently an alkyl, aryl, aralkyl, alkaryl, or a group of formula $-R^6-(OR^6)_n-OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero.

In a third aspect, a crosslinkable composition is provided. The crosslinkable composition contains a) a polymeric material of Formula (II) as described above in the first aspect and b) a second monomer composition comprising a crosslinking monomer having at least two ethylenically unsaturated groups.

In a fourth aspect, a crosslinked composition is provided. The crosslinked composition contains a cured product of a crosslinkable composition as described above in the third aspect.

In a fifth aspect, an article is provided that includes a first substrate and a polymeric material layer positioned adjacent to the first substrate. The polymeric material is of Formula (II) as described above in the first aspect.

In a sixth aspect, an article is provided that includes a first substrate and a crosslinkable composition layer adjacent to the first substrate. The crosslinkable composition layer contains the crosslinkable composition described above in the third aspect.

In a seventh aspect, another article is provided that includes a first substrate and a crosslinked composition layer adjacent to the first substrate. The crosslinked composition layer contains the crosslinked composition described above in the fourth aspect.

DETAILED DESCRIPTION

Figure 1:
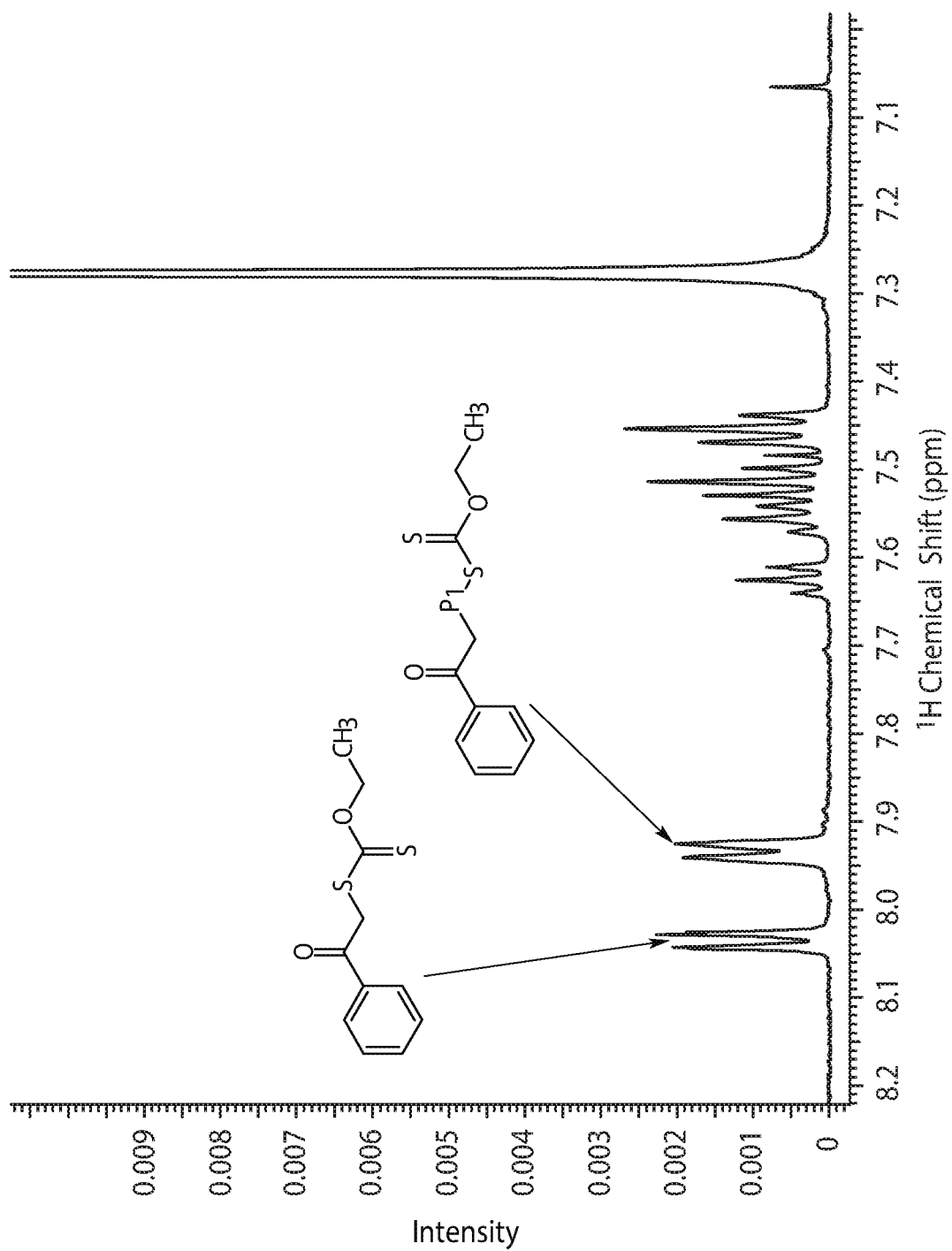
FIG. 1 shows the aromatic region of the $^1$H NMR spectrum for Comparative Example 7 after 84 percent conversion of the monomer.

Controlled radical initiators that are ketone-containing dithiocarbamate or dithiocarbonate compounds are used to form polymeric materials that have one or more polymeric blocks. Reaction mixtures containing controlled radical initiators and various ethylenically unsaturated monomers, polymeric materials formed from the reaction mixtures, crosslinkable compositions containing the polymeric materials, crosslinked compositions formed from the crosslinkable compositions, and articles containing the polymeric materials, the crosslinkable compositions, or the crosslinked compositions are provided.

The controlled radical initiator compounds can be referred to as iniferters because they can function as a controlled radical initiator, transfer agent, and terminator. The controlled radical initiators can be referred to as photoinitiators or photoiniferters because the controlled radical polymerization reaction typically is photolytically induced. The resulting polymeric material formed from the controlled radical initiators typically have a terminal thiocarbamate or thiocarbonate group as well as a terminal ketone group.

The polymeric materials having well controlled architectures can be formed using these controlled radical initiator compounds. The polymeric materials can be homopolymers, random copolymers, or block copolymers. Crosslinkable compositions can be prepared that contain the polymeric materials and a monomer composition that includes a crosslinking monomer having at least two ethylenically unsaturated groups. When the crosslinkable composition is exposed to actinic radiation (e.g., radiation in the ultraviolet region of the electromagnetic spectrum), the polymeric material undergoes chain extension and crosslinking reactions.

The terms "a", "an", and "the" are used interchangeably with "at least one" to mean one or more of the elements being described.

The term "and/or" means either or both. For example, "A and/or B" means only A, only B, or both A and B.

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like.

The term "alkyl" refers to a monovalent group that is a radical of an alkane. The alkyl group can have 1 to 32 carbon atoms, 1 to 20 carbon atoms, 1 to 12 carbon atoms, or 1 to 6 carbon atoms. The alkyl can be linear, branched, cyclic, or a combination thereof. A linear alkyl has at least one carbon atoms while a cyclic or branched alkyl has at least 3 carbon atoms. In some embodiments, if there are greater than 12 carbon atoms, the alkyl is branched.

The term "alkoxy" refers to a monovalent group of formula —OR$^a$ where R$^a$ is an alkyl as defined above.

The term "alkylene" refers to a divalent group that is a radical of an alkane. The alkylene group can have 1 to 32 carbon atoms, 1 to 20 carbon atoms, 1 to 12 carbon atoms, or 1 to 6 carbon atoms. The alkylene can be linear, branched, cyclic, or a combination thereof. A linear alkylene has at least one carbon atoms while a cyclic or branched alkylene has at least 3 carbon atoms. In some embodiments, if there are greater than 12 carbon atoms, the alkylene is branched.

The term "aryl" refers to a monovalent group that is a radical of an aromatic carbocyclic compound. The aryl group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms or 6 to 10 carbon atoms.

The term "aryloxy" refers to a monovalent group that is of formula —O—Ar where Ar is an aryl group as defined above. The term "aralkyl" refers to an alkyl group substituted with at least one aryl group. That is, the aralkyl group is of formula —R$^d$—Ar where R$^d$ is an alkylene and Ar is an aryl. The aralkyl group contains 6 to 40 carbon atoms. The aralkyl group often contains an alkylene group having 1 to 20 carbon atoms or 1 to 10 carbon atoms and an aryl group having 5 to 20 carbon atoms or 6 to 10 carbon atoms.

The term "aralkyloxy" refers to a monovalent group of formula —O—R$^d$—Ar where R$^d$ and Ar are defined above for an aralkyl.

The term "alkenyl" refers to a monovalent group that is a radical of an alkene, which is a compound having at least one carbon-carbon double bond. In some embodiments, the alkenyl has a single carbon-carbon double bond. In some more specific embodiments, the alkenyl has a terminal ethylenically unsaturated group. The alkenyl can be linear, branched, or cyclic. The alkenyl has 2 to 20 carbon atoms, 2 to 10 carbon atoms, or 2 to 6 carbon atoms.

The term "alkenyloxy" refers to a monovalent group of formula —OR$^b$ where R$^b$ is an alkenyl as defined above.

The term "heteroalkyl" refers to an alkyl group where at least one of the catenated carbon atoms is replaced with oxy, thio, or —NH—. The term "heterocyclic ring" refers to a ring structure having at least 1 heteroatom selected from oxygen, nitrogen, or sulfur, wherein the ring structure is saturated or unsaturated. The heterocyclic ring typically has 5 to 7 ring atoms and 1 to 3 heteroatoms. The heterocyclic ring can optionally be fused to one or more additional rings that are carbocyclic or heterocyclic and that can be saturated or unsaturated. Any of the rings can optionally be substituted with an alkyl group.

The term "ketone group" refers to a carbonyl group that is bonded to two carbon atoms (i.e., the carbonyl group is between two carbon atoms).

The term "(meth)acryloyl" refers to a group of formula $CH_2=CHR^c(CO)$— where $R^c$ is hydrogen or methyl and the group —(CO)— refers to a carbonyl group.

The term "(meth)acrylate" refers to an acrylate, a methacrylate, or both. Likewise, the term "(meth)acrylamide" refers to an acrylamide, a methacrylamide, or both and the term "(meth)acrylic acid" refers to acrylic acid, methacrylic acid, or both.

The terms "in a range of" or "in the range of" are used interchangeably to refer to all values within the range plus the endpoints of the range.

Various polymeric materials are formed from a reaction mixture that includes both (a) a photoinitiator of Formula (I)

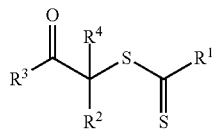

(I)

and (b) a first monomer composition containing at least one first monomer having a single ethylenically unsaturated group. The molar ratio of the first monomer (e.g., the ethylenically unsaturated groups in the first monomer composition) to the photoinitiator of Formula (I) is selected to form polymeric material upon exposure to actinic radiation in the ultraviolet region of the electromagnetic spectrum.

In Formula (I), group $R^1$ is an alkoxy, aralkyloxy, alkenoxy or $—N(R^5)2$. Group $R^2$ and $R^3$ are each independently an alkyl, aryl, aralkyl, alkaryl, or a group of formula $—R^6—(OR^6)_n—OR^7$; alternatively, groups $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero.

In some embodiments of Formulas (I), group $R^1$ is an alkoxy, aralkyloxy, or alkenoxy. Such photoinitiators are of Formula (I-A) where $—OR^{10}$ is an alkyloxy, aralkyloxy, or alkenoxy (i.e., $R^{10}$ is an alkyl, aralkyl, or alkenyl).

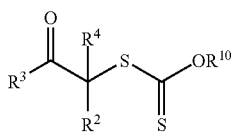

(I-A)

These photoinitiators are dithiocarbonate compounds having a ketone group.

Suitable alkoxy groups for $R^1$ of Formula (I) and for $—OR^{10}$ of Formula (I-A) typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkoxy groups have 1 to 20 carbon atoms, 1 to 10 carbon atoms, 2 to 10 carbon atoms, 1 to 6 carbon atoms, 2 to 6 carbon atoms, or 1 to 4 carbon atoms. Suitable aralkyloxy groups for $R^1$ and for $—OR^{10}$ typically contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyloxy group is often phenyl. Suitable alkenoxy groups for $R^1$ and for $—OR^{10}$ typically have at least 2 carbon atoms, at least 3 carbon atoms, or at least 4 carbon atoms and can have up to 20 carbon atoms, up to 18 carbon atoms, up to 16 carbon atoms, up to 12 carbon atoms, up to 10 carbon atoms, or up to 6 carbon atoms. Some example alkenoxy groups have 2 to 20 carbon atoms, 2 to 10 carbon atoms, 2 to 8 carbon atoms, 2 to 6 carbon atoms, or 2 to 4 carbon atoms. In many embodiments, $R^{10}$ in Formula (I-A) is an alkyl (i.e., group $—OR^{10}$ is an alkoxy in Formula (I-A); this corresponds to group $R^1$ being an alkoxy in Formula (I)).

In other embodiments of Formula (I), group $R^1$ is of formula $—N(R^5)_2$. Such photoinitiators are of Formula (I-B).

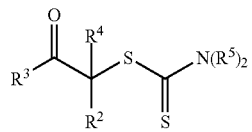

(I-B)

These photoinitiators are dithiocarbamate compounds having a ketone group.

Each $R^5$ in Formula (I-B) is an alkyl or two adjacent $R^5$ groups combine with the nitrogen to which they are both attached to form a first heterocyclic ring having at least one heteroatom selected from nitrogen, oxygen, and sulfur, the first heterocyclic ring being saturated or unsaturated (e.g., partially or fully unsaturated) and optionally fused to one or more second rings that are carbocyclic or heterocyclic. Suitable alkyl groups typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms. When the formula $—N(R^5)_2$ forms a first heterocyclic ring, the heterocyclic ring typically has a first ring structure with 5 to 7 ring members or 5 to 6 ring members and with 1 to 3 heteroatoms or 1 to 2 heteroatoms in the ring. If there is one heteroatom in the first ring structure, the heteroatom is nitrogen. If there are two or three heteroatoms in the first ring structure, one heteroatom is nitrogen and any additional heteroatom is selected from nitrogen, oxygen, and sulfur. The first ring optionally can be fused to one or more second ring structures that are heterocyclic or carbocyclic and saturated or unsaturated (e.g., partially or fully unsaturated). If the second ring structure is heterocyclic, it typically has 5 to 7 or 5 to 6 ring members and 1, 2, or 3 heteroatoms selected from nitrogen, oxygen, and sulfur. If the second ring structure is carbocyclic, it is often benzene or a saturated ring having 5 or 6 ring members. In many embodiments, the heterocyclic ring has a single ring structure with 5 or 6 ring members and with either 1 or 2 heteroatoms in the ring. Examples of heterocyclic rings include, but are not limited to, morpholino, thiomorpholino, pyrrolidinyl, piperidinyl, homo-piperidinyl, indolyl, carbazolyl, imidazolyl, and pyrazolyl. In many embodiments of Formula (I-B), $R^5$ is an alkyl. Groups $R^2$ and $R^3$ in Formula (I) (including Formulas (I-A) and (I-B)) are an alkyl, aryl, aralkyl, alkaryl, or a group of formula —$R^6$—$(OR^6)_n$—$OR^7$; alternatively, groups $R^2$ and $R^3$ combine to form a ring structure that includes the carbonyl group. When $R^2$ and/or $R^3$ is an alkyl, the alkyl group typically has at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms. When $R^2$ and/or $R^3$ is an aryl, the aryl often has 5 to 12 carbon atoms, 6 to 12 carbon atoms, or 6 to 10 carbon atoms. The aryl is often phenyl. When $R^2$ and/or $R^3$ is an aralkyl, the aralkyl group often contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyl group is often phenyl. When $R^2$ and/or $R^3$ is an alkaryl, the alkaryl group often contains an arylene group having 5 to 12 carbon atoms, 6 to 12 carbon atoms, or 6 to 10 carbon atoms and an alkyl group having 1 to 10 carbon atoms, 2 to 10 carbon atoms, 1 to 6 carbon atoms, 2 to 6 carbon atoms, or 1 to 4 carbon atoms. When $R^2$ and/or $R^3$ is of formula —$R^6$—$(OR^6)_n$—$OR^7$, each $R^6$ is an alkylene having 1 to 10 carbon atoms, 1 to 6 carbon atoms, or 1 to 4 carbon atoms, each $R^7$ is an alkyl having 1 to 10 carbon atoms, 1 to 6 carbon atoms, or 1 to 4 carbon atoms, and n is an integer equal to at least 0, at least 1, at least 2 and up to 10, up to 8, up to 6, up to 4, or up to 2. When $R^2$ and $R^3$ combine to form a ring structure that includes the carbonyl group, the ring structure typically has 4, 5, 6, or 7 ring members. The number of ring members is often 5 or 6. The ring structure can be saturated or unsaturated but is often saturated. The ring members are typically carbon. For example, $R^2$ and $R^3$ can combine to be an alkylene group. Suitable alkylene groups typically have 3 or 4 carbon atoms.

In some embodiments, $R^2$ is an alkyl.

Group $R^4$ is an alkyl or hydrogen. Suitable alkyl groups usually have 1 to 10 carbon atoms, 1 to 6 carbon atoms, or 1 to 4 carbon atoms. Group $R^4$ is often hydrogen.

The photoinitiator compounds of Formula (I) can be formed by any suitable method. One suitable method is shown in Reaction Scheme A.

Reaction Scheme A

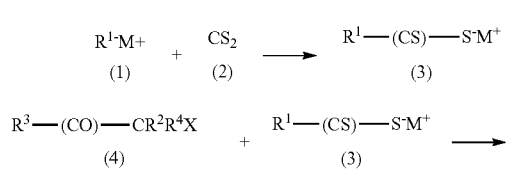

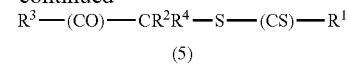

(5)

In this reaction scheme, a halo ketone compound (compound (4) where X is a halo) is reacted with a compound of formula R'—(CS)—S⁻M⁺, which is compound (3) as shown in Reaction II. Compound (3) can be formed, for example, by treating a salt of formula (1) with carbon disulfide (Reaction I). Compound (1) is a salt of an alkoxide, aryloxide, or amine where M+ is an alkali metal, a tetralkyl ammonium ion, a trialkyl ammonium ion, or a dialkylammonium ion. Reaction I is often conducted at temperatures between about 0° C. and about 80° C., in the presence of an organic solvent such as acetone, acetonitrile, or an alcohol. The reaction (Reaction II) of compound (4) with compound (3) is typically conducted at temperatures between about 0° C. and about 80° C., in the presence of an organic solvent such as acetone, acetonitrile, or an alcohol.

In some examples of Reaction Scheme A, commercially available compounds of formula $R^3$—(CO)—$CR^2R^4X$ (compound (4)) include 3-chloro-2-butanone, 1-chloro-1-methoxy-propan-2-one, 2-bromo-1-phenyl-propan-1-one, desyl chloride (2-chloro-2-phenylacetophenone), desyl bromide, 2-bromo-1-phenyl-propan-1-one, 2-chlorocyclopentanone, and 2-chlorocyclohexanone. Examples of compound (3) include, but are not limited to, sodium diethyldithiocarbamate trihydrate and various xanthate salts such as potassium ethyl xanthate, sodium ethyl xanthate, potassium isopropyl xanthate, sodium isopropyl xanthate, and potassium amyl xanthate.

Some specific photoinitiators of Formula (I) include carbonodithioic acid O-(isopropyl) S-(1-methyl-2-oxopropyl) ester, carbonodithioic acid O-(isopropyl) S-(1,1-dimethyl-2-oxopropyl) ester, carbonodithioic acid O-(isopropyl) S-(1-methoxy-2-oxopropyl) ester, carbonodithioic acid, O-isopropyl S-(1-methyl-2-oxo-2-phenylethyl) ester, carbonodithioic acid, O-isopropyl S-(1-phenyl-2-oxo-2-phenylethyl) ester, and carbonodithioic acid, N-diethyl S-(1-methyl-2-oxo-2-phenylethyl) ester.

The photoinitiator of Formula (I) (including those of Formulas (I-A) and (I-B)) is mixed with one or more monomers (e.g., first monomers) having a single ethylenically unsaturated group (e.g., a first monomer composition) to form a polymeric material of Formula (II).

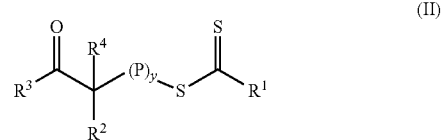

In Formula (II), groups $R^1$, $R^2$, $R^3$, and $R^4$ are the same as defined for the photoinitiator of Formula (I). Each P is a polymeric block that includes a polymerized product of a first monomer composition containing at least one first monomer having a single ethylenically unsaturated group, y is an integer equal to at least 1 (e.g., in a range of 1 to 10, in a range of 1 to 5, or in a range of 1 to 3). The variable y refers to the number of polymeric blocks. That is, $(P)_y$ means that there are y polymeric blocks P. The molecular weight of each polymeric block can be the same or different.

Each polymeric block P in Formula (II) is the polymerized product of a monomer composition containing at least one monomer having a single ethylenically unsaturated group. Any monomer having a single ethylenically unsaturated group can be used based on the desired properties of the resulting polymeric material. In some embodiments, all the monomers used to form any polymeric block P have a single (meth)acryloyl group. In other embodiments, all the monomers used to form any polymeric block P have a single ethylenically unsaturated group that is not a (meth)acryloyl group. In still other embodiments, all the monomers used to form any polymeric block P have a single ethylenically unsaturated group and some, but not all, of the ethylenically unsaturated groups are (meth)acryloyl groups. Each polymeric block can be a homopolymer or a copolymer. Any monomer can be used alone or in combination with other monomers to form each polymeric block.

Suitable monomers with a single (meth)acryloyl group that can be used to form the polymeric material of Formula (II) include, but are not limited to, alkyl (meth)acrylates, fluorinated alkyl (meth)acrylates, aryl (meth)acrylates, aralkyl (meth)acrylates, substituted aryl (meth)acrylates, (meth)acrylic acid, (meth)acrylamide, N-alkyl (meth)acrylamides, N,N-dialkyl (meth)acrylamides, N-alkylaminoalkyl (meth)acrylates, N,N-dialkylaminoalkyl (meth)acrylates, N-alkylaminoalkyl (meth)acrylamides, N,N-dialkylaminoalkyl (meth)acrylamides, hydroxy-substituted alkyl (meth)acrylates, hydroxy-substituted alkyl (meth)acrylamides, alkoxylated alkyl (meth)acrylates, acid-substituted alkyl (meth)acrylates, acid-substituted alkyl (meth)acrylamides, glycidyl-containing (meth)acrylates, isocyanate-containing (meth)acrylates such as isocyanate-substituted alkyl (meth)acrylates, aminosulfonyl-containing (meth)acrylates, cationic monomers such as N,N,N-trialkylaminoalkyl (meth)acrylates, zwitterionic monomers (e.g., 2-(N-3-sulfopropyl-N,N-dimethylammonium)ethyl (meth)acrylate), and mixtures thereof. A plurality of different monomers having a single (meth)acryloyl group can be included in the monomer composition for any polymeric block.

In other embodiments, the reaction mixture used to form any block P in the polymeric material of Formula (II) includes a monomer composition containing a monomer having a single ethylenically unsaturated group that is not a (meth)acryloyl group. Suitable such monomers include, but are not limited to, N-vinylpyrrolidone, N-vinylcaprolactam, vinyl acetate, vinyl methyl ether, vinyl-2-ethylhexanoate, vinyl neodecanoate, styrene, isoprene, butadiene, vinyl dimethylazlactone (VDM), isopropenyl dimethylazlactone (IDM), and vinyl oxazole, and the like.

In Formula (II), the variable y refers to the number of polymeric blocks P. The variable y is an integer equal to at least 1 (e.g., in a range of 1 to 10, in a range of 1 to 5, in a range of 1 to 3, or in a range of 1 to 2). Often y is equal to 1, 2, or 3.

Some polymeric materials of Formula (II) are formed from the photoinitiators of Formula (I-A) and are of Formula (II-A).

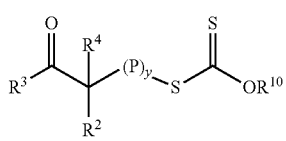

In Formula (II-A), group $R^{10}$ is the same as defined in Formula (I-A). Groups $R^2$, $R^3$, $R^4$, P, and the variable y are the same as defined in Formula (II).

Some polymeric materials of Formula (II) are formed from the photoinitiators of Formula (I-B) and are of Formula (II-B).

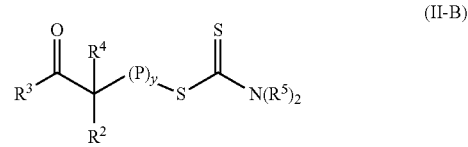

In Formula (II-B), groups $R^2$, $R^3$, $R^4$, $R^5$, P, and variable y are the same as defined in Formulas (I-B) and (II). In some embodiments of the polymeric material of Formula (II-B), each $R^5$ is an alkyl.

While not wishing to be bound by theory, it is believed that polymerization occurs as shown in Reaction Scheme B to form a material where y is equal to 1.

Reaction Scheme B

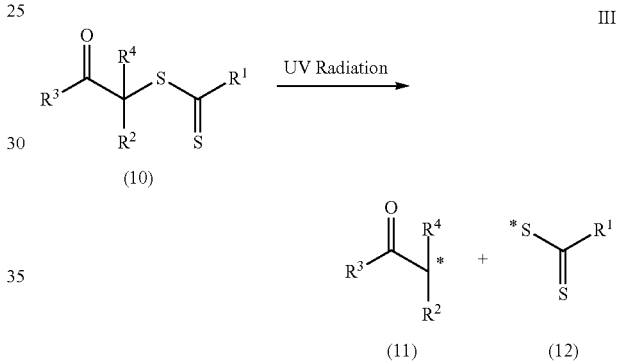

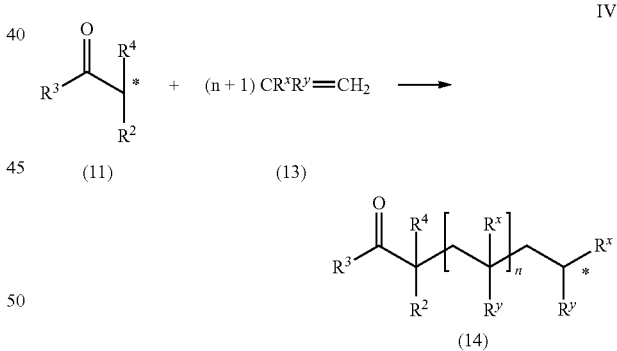

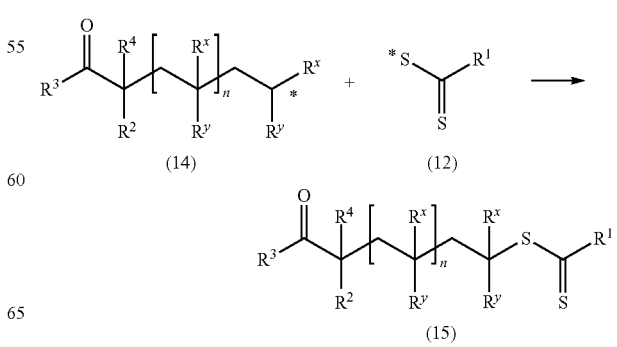

-continued

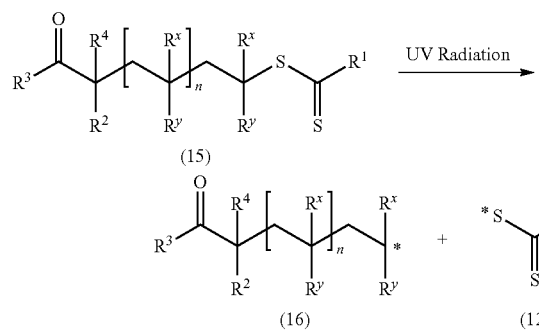

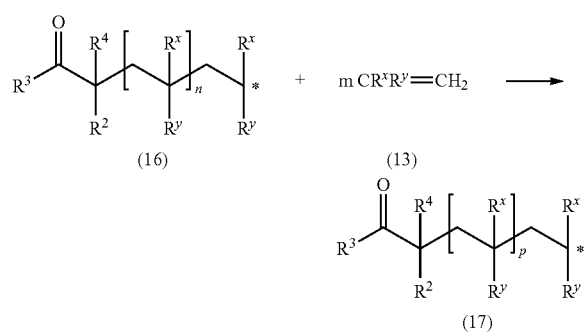

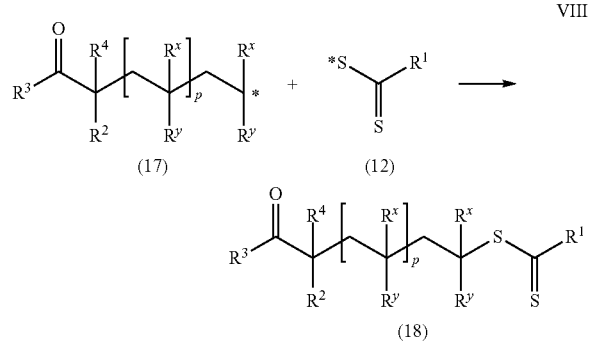

In Reaction Scheme B, the photoinitiator of Formula (I), which is shown as compound (10), undergoes photolysis of one of the C—S bonds when exposed to actinic radiation (e.g., ultraviolet radiation) (Reaction III). Two different radicals, radical (11) and radical (12), are formed in Reaction III. In Reaction IV, radical (11) reacts with ethylenically unsaturated monomers (compound (13). The monomers polymerize and radical (14) is formed. Radical (14) can combine with radical (12) and the polymerization reaction is terminated. The resulting polymeric material of Reaction V is compound (15). Compound (15) can undergo photolysis of the C—S bond in the presence of actinic radiation (e.g., ultraviolet radiation). Photolysis can result in the generation of radical (12) and radical (16) as shown in Reaction VI. In Reaction VII, radical (16) reacts with ethylenically unsaturated monomers (compound 13). The monomers polymerize and radical (17) is formed. The variable p is equal to the sum (m+n). Radical (17) can combine with radical (12) and the polymerization reaction is terminated. The resulting polymeric material formed in Reaction VIII is compound (18). While exposure to actinic radiation (e.g., ultraviolet radiation) continues, photolysis of compound (18) can occur and additional monomeric units can be added. When exposure to actinic radiation (e.g., ultraviolet radiation) is terminated, no further photolysis can occur and no additional monomeric units can be added.

In Reaction Scheme B, compound (13) is a monomer having a single ethylenically unsaturated group. If the ethylenically unsaturated group is a (meth)acryloyl group, $R^x$ is hydrogen or methyl and $R^y$ includes a group —(CO)—X—$R^{11}$. Group X is oxy or —$NR^{12}$— where $R^{12}$ is hydrogen or alkyl. Group $R^{11}$ is the remainder of the (meth)acryloyl-containing monomer. That is, the monomer is of formula $H_2C=CR^x$—(CO)—X—$R^{11}$. Group $R^x$ is hydrogen or methyl and group $R^{11}$ is the remainder, for example, of any (meth)acrylate or (meth)acrylamide monomer described herein.

Polymeric materials of Formula (II) with y equal to 1 can be formed by mixing a photoinitiator of Formula (I) with a monomer composition 1A and exposing the resulting reaction mixture 1A to actinic radiation (e.g., ultraviolet light). The actinic radiation exposure causes the photolysis of the photoinitiator and permits controlled radical polymerization of the monomer composition 1A to form a first polymeric block. When exposure to actinic radiation is terminated, the first polymerization reaction ceases. The product of the first polymerization is a polymeric material of Formula (II-1) where $P^1$ is the first polymeric block.

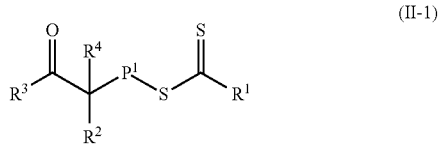

To form a polymeric block, the molar ratio of the monomers (e.g., the ethylenically unsaturated groups) to the photoinitiator of Formula (I) is at least 3, at least 10, at least 50, at least 100, at least 500, or at least 1000.

Another monomer composition, referred to as monomer composition 1B, can be added to the product of the reaction mixture 1A (i.e., the polymeric material of Formula (II-1)) to form a reaction mixture 1B. Upon exposure of the reaction mixture 1B to actinic radiation, photolysis occurs again releasing the radical of formula $R^1$—(CS)—S*. Monomer composition 1B can polymerize to form a second polymeric block $P^2$ attached to the end of any polymeric block $P^1$ in the polymeric material of Formula (II-1). When exposure to actinic radiation is terminated, the second polymerization reaction ceases. The size (e.g., molecular weight) of the two polymeric blocks ($P^1$ and $P^2$) can be the same or different. The product of the second polymerization is the polymeric material of Formula (II-2), which corresponds to Formula (II) where y is equal to 2 (there are two polymeric blocks P and these polymeric blocks are $P^1$ and $P^2$).

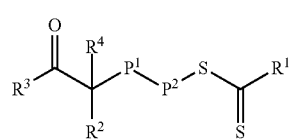

This process can be repeated as many times as desired to add additional polymeric blocks. For example, if y is equal to 3 in the polymeric material of Formula (II), there are three polymeric blocks. Such a polymeric material is of Formula (II-3) where $P^3$ is a third polymeric block.

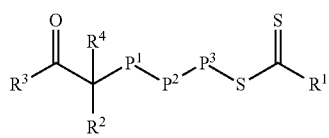

Each polymeric block (e.g., P, $P^1$, $P^2$ or $P^3$) can have any desired molecular weight. The molecular weight of each block can be the same or different than any other polymeric block. In some embodiments, the weight average molecular weight of any polymeric block is at least 500 Daltons, at least 1,000 Daltons, at least 2,000 Daltons, at least 5,000 Daltons, at least 10,000 Daltons, at least 20,000 Daltons, at least 50,000 Daltons, or at least 100,000 Daltons. The weight average molecular weight of any polymeric block can be up to 1 million Daltons or even higher, up to 750,000 Daltons, up to 500,000 Daltons, up to 200,000 Daltons, or up to 100,000 Daltons. In some embodiments, the polymeric material of Formula (II) has an overall weight average molecular weight in a range of 10,000 Daltons to 5 million Daltons, in a range of 10,000 Daltons to 3 million Daltons, or in a range of 10,000 Daltons to 1 million Daltons.

For polymeric materials having multiple polymeric blocks, different monomer compositions are typically used for each polymeric block. For example, the first polymeric block $P^1$ is a polymerized product of a monomer composition 1A containing at least one monomer having a single ethylenically unsaturated group. $P^2$ is a second polymeric block that is a polymerized product of a monomer composition 1B containing at least one monomer having a single ethylenically unsaturated group. The composition of the second polymeric block $P^2$ is different than the composition of the first polymeric block $P^1$. If another polymeric block $P^3$ is added that is a polymerized product of a monomer composition 1C, the composition of the third block is usually selected to be different than the second polymeric block $P^2$ and can be selected to be the same as or different than the composition of the first polymeric block $P^1$. Stated differently, monomer composition 1A is different than monomer composition 1B and monomer composition 1B is different than monomer composition 1C. Monomer composition 1A can be the same or different than monomer composition 1C. Each polymeric block can be a homopolymer or a copolymer. If any block is a copolymer, it is typically a random copolymer.

To form a polymeric material of Formula (II) where y is equal to 1, the photoinitiator of Formula (I) is mixed with a monomer composition 1A (i.e., first monomer composition 1A) to form a reaction mixture 1A (i.e., first reaction mixture 1A). Exposing reaction mixture 1A to actinic radiation (e.g., ultraviolet radiation) causes photolysis of the photoinitiator and permits controlled radical polymerization of the monomer composition 1A. When exposure to actinic radiation (e.g., ultraviolet radiation) is terminated, the polymerization reaction ceases. The product of reaction mixture 1A is a polymeric material of Formula (II-1).

More specifically, to prepare a polymeric material of Formula (II-1), monomer composition 1A (e.g., a first monomer composition) is mixed with a photoinitiator of Formula (I) to form reaction mixture 1A. Reaction mixture 1A can be neat (i.e., no solvent is present) or can be mixed with a solvent that dissolves both the monomer composition 1A and the photoinitiator of Formula (I). Any solvent that is added is usually selected so that the growing polymeric material is also soluble. In some embodiments, the percent solids in reaction mixture 1A is at least 10 weight percent, at least 20 weight percent, at least 30 weight percent, or at least 40 weight percent and up to 100 weight percent, up to 80 weight percent, or up to 60 weight percent. The amount of solvent added is often selected based on the desired viscosity, particularly the viscosity of the final polymerized material. The desired viscosity is usually sufficiently low so that the final polymeric material can be readily processed and/or applied to a substrate. As used herein, the term "weight percent solids" refers to the weight percent of the composition that is not a solvent. That is, the monomers and the polymeric material are considered to be solids even if dissolved in the composition.

If a solvent is added, the solvent is often an ester (e.g., ethyl acetate, butyl acetate, and ethylene glycol monomethyl ether acetate), an ether (e.g., dimethyl ether, diethyl ether, ethyl propyl ether, dipropyl ether, methyl t-butyl ether, di-t-butyl ether, dimethoxy ethane, 2-methoxyethanol, diethylene glycol dimethyl ether, dioxane, and tetrahydrofuran), acetonitrile, methylene chloride, an aromatic hydrocarbon (e.g., benzene, xylene, and toluene), or a ketone (e.g., acetone, methyl ethyl ketone, methyl isobutyl ketone, cyclopentanone, and cyclohexanone). Mixtures of solvents can be used. Further, one or more solvents can be combined with water, if miscible. Polymerization of the monomer composition 1A can start at room temperature (e.g., about 20° C. to 25° C.) but can also start, if desired, at higher or lower temperatures.

Reaction mixture 1A is exposed to actinic radiation (e.g., ultraviolet radiation) to activate the photoinitiator of Formula (I) and commence controlled radical polymerization of monomer composition 1A. The resulting polymeric block $P^1$ can be a homopolymer or a random copolymer.

Unless the polymeric material will be crosslinked with a crosslinking monomer having at least two ethylenically unsaturated groups, polymerization of reaction mixture 1A is usually allowed to proceed until greater than 80 weight percent, greater than 85 weight percent, greater than 90 weight percent, greater than 95 weight percent, greater than 98 weight percent, greater than 99 weight percent, or 100 weight percent of the monomers in the monomer composition 1A have undergone controlled radical polymerization. Alternatively, unreacted monomers can be removed from the polymerized material. One of skill in the art is familiar with methods of separating the polymeric material from residual monomers.

Alternatively, if the polymeric material will be crosslinked with a monomer having at least two ethylenically unsaturated groups, polymerization of reaction mixture 1A can be allowed to proceed to any desired extent until at least 5 weight percent of the monomer composition 1A has undergone controlled radical polymerization. For example, the polymerization reaction can proceed until at least 10 weight percent, at least 20 weight percent, at least 30 weight percent, at least 40 weight percent and up to 100 weight percent, up to 99 weight percent, up to 98 weight percent, up to 95 weight percent, up to 90 weight percent, up to 85 weight percent, up to 80 weight percent, up to 70 weight percent, up to 60 weight percent, or up to 50 weight percent of the monomer composition 1A has undergone controlled radical polymerization. The resulting polymeric material can be combined with a second monomer composition containing a crosslinking monomer having at least two ethylenically unsaturated groups to form a crosslinkable composition.

Advantageously, the photoinitiators of Formula (I) are very efficient. During the early stages of polymerization many polymeric chains are initiated and the average molecular weight (both number average and weight average molecular weights) of the formed polymeric material is low. As the polymerization reaction progresses, the average molecular weight tends to increase. In contrast, with many other photoinitiators, even those having both a group of formula —S—(CS)—$R^1$ and a ketone group such as photoinitiators PI-1, PI-2, and PI-3 in the Example section, during the early stages of polymerization only a few polymeric chains are initiated and the average molecular weight (both number average and weight average molecular weights) of the formed polymeric material is high compared to that of polymeric materials formed using the photoinitiators of Formula (I). For these other photoinitiators, as the polymerization reaction progresses, the average molecular weight tends to decrease.

More specifically, the selection of the group adjacent to the —S—(CS)—$R^1$ group in Formula (I) impacts the efficiency of the polymerization. In Formula (I), this group is equal to —$CR^2R^4$— where $R^2$ and $R^4$ are defined above. Compounds where this group is not present (e.g., photoinitiators PI-1 and PI-2 in the Example section), typically do not result in the steady increase in the molecular weight during the polymerization process.

Polymeric materials having more than one polymeric block can be formed from the polymeric material of Formula (II-1). A monomer composition 1B can be added to the polymeric material of Formula (II-1) to form reaction mixture 1B. Upon exposure of reaction mixture 1B to actinic radiation (e.g., ultraviolet radiation), photolysis occurs again releasing the radical of formula $R^1$—(CS)—S*. Monomer composition 1B can polymerize to form a second polymeric block $P^2$ attached to a first polymeric block $P^1$ in the polymeric material of Formula (II-1). When exposure to actinic radiation (e.g., ultraviolet radiation) is terminated, the polymerization reaction ceases. The product of the reaction mixture 1B is the polymeric material of Formula (II-2).

More specifically, a polymeric material of Formula (II-2) can be formed from the polymeric material of Formula (II-1). After 80 weight percent or more (such as, at least 90 weight percent, at least 95 weight percent, at least 98 weight percent, at least 99 weight percent, or 100 weight percent) of the monomer composition 1A has undergone controlled radical polymerization, the polymerization reaction is stopped by terminating exposure to actinic radiation (e.g., ultraviolet radiation). A reaction mixture 1B is formed by adding a monomer composition 1B to the reaction product of the reaction mixture 1A. The reaction mixture 1B includes a first polymeric material of Formula (II) plus a monomer composition 1B having at least one monomer with a single ethylenically unsaturated group. It is typically not necessary to add further photoinitiator of Formula (I) to reaction mixture 1B.

Any optional solvent that is included in reaction mixture 1B is usually selected so that it solubilizes the first polymeric material of Formula (II-1), the photoinitiator of Formula (I), and monomer composition 1B. That is, reaction mixture 1B is typically a single phase. In some embodiments, the percent solids in reaction mixture 1B is selected to have percent solids equal to at least 10 weight percent, at least 20 weight percent, at least 30 weight percent, or at least 40 weight percent and up to 100 weight percent (i.e., no solvent is added), up to 80 weight percent, or up to 60 weight percent. Suitable solvents are the same as those discussed above for reaction mixture 1A. The amount of solvent added is selected based on the desired viscosity, particularly the viscosity of the final polymerized material. The desired viscosity is usually sufficiently low so that the final polymeric material can be readily processed and/or applied to a substrate.

Reaction mixture 1B is exposed to actinic radiation (e.g., ultraviolet radiation) to commence controlled radical polymerization of monomer composition 1B. Polymerization of the second monomer composition can occur at room temperature (e.g., about 20° C. to 25° C.) but can also occur, if desired, at higher or lower temperatures.

Unless the polymeric material will be crosslinked with a crosslinking monomer having at least two ethylenically unsaturated groups, the polymerization of reaction mixture 1B is usually allowed to proceed until greater than 80 weight percent, greater than 85 weight percent, greater than 90 weight percent, greater than 95 weight percent, greater than 98 weight percent, greater than 99 weight percent, or 100 weight percent of the monomers in the monomer composition 1B have undergone controlled radical polymerization. Alternatively, unreacted monomers can be removed from the polymerized material. One of skill in the art is familiar with methods of separating the polymeric material from residual monomers.

If the polymeric material will be crosslinked with a crosslinking monomer having at least two ethylenically unsaturated groups, polymerization of reaction mixture 1B can be allowed to proceed to any desired extent until at least 5 weight percent of the monomer composition 1B has undergone controlled radical polymerization. For example, the polymerization reaction can proceed until at least 10 weight percent, at least 20 weight percent, at least 30 weight percent, at least 40 weight percent and up to 100 weight percent, up to 99 weight percent, up to 98 weight percent, up to 95 weight percent, up to 90 weight percent, up to 85 weight percent, up to 80 weight percent, up to 70 weight percent, up to 60 weight percent, or up to 50 weight percent of the monomer composition 1B has undergone controlled radical polymerization. The resulting polymeric material can be combined with a second monomer composition containing a crosslinking monomer having at least two ethylenically unsaturated groups to form the crosslinkable composition.

The composition of polymeric block $P^2$ is typically different than the composition of polymeric block $P^1$. In some embodiments, the polymeric blocks $P^1$ and $P^2$ have different glass transition temperatures as measured by Differential Scanning Calorimetry. In some embodiments, the difference in the glass transition temperature of polymeric blocks $P^1$ and $P^2$ is at least 40° C., at least 50° C., at least 60° C., at least 70° C., at least 80° C., at least 90° C., or at least 100° C. It is often preferable, that the polymeric material of Formula (II) is soluble in reaction mixture 1B containing monomer composition 1B used to form the polymeric material of Formula (III).

In some embodiments, it is desirable to have sharp transitions between the first polymeric block $P^1$ and the second polymeric blocks $P^2$. The transition between two polymeric blocks can be controlled by the percent conversion of reaction mixture 1A to the first polymeric block. If the percent conversion is relatively low (e.g., less than 90 percent), then reaction mixture 1B will include a mixture of the monomer composition 1B plus remaining unreacted monomer composition 1A. That is, some of the monomers from monomer composition 1A will be in the second polymeric block $P^2$. To minimize the presence of monomeric units of monomer composition 1A in the second polymeric block $P^2$, the percent conversion of monomer composition 1A should be maximized. A higher percent conversion must be balanced, however, against a longer reaction time. Alternatively, the transition between two polymeric blocks can be controlled by removal of unreacted monomers from the polymerized material. One of skill in the art is familiar with methods of separating the polymeric material from residual monomers.

Polymeric material of Formula (II-3) can be formed from the polymeric material of Formula (II-2). After 80 weight percent or more (such as, at least 90 weight percent, at least 95 weight percent, at least 98 weight percent, at least 99 weight percent, or 100 weight percent) of the monomer composition 1B used to form the polymer of Formula (II-2) has undergone controlled radical polymerization, the polymerization reaction is stopped by terminating exposure to actinic radiation (e.g., ultraviolet radiation). Reaction mixture 1C is formed by adding monomer composition 1C to the reaction product of the reaction mixture 1B. Reaction mixture 1C includes a second polymeric material of Formula (II-2) plus a monomer composition 1C having at least one monomer with a single ethylenically unsaturated group.

Any optional solvent that is included in reaction mixture 1C is usually selected so that it solubilizes the polymeric material of Formula (II-2), the photoinitiator of Formula (I), and the monomer composition 1C. That is, reaction mixture 1C is typically a single phase. In some embodiments, the percent solids in reaction mixture 1C is selected to have percent solids equal to at least 10 weight percent, at least 20 weight percent, at least 30 weight percent, or at least 40 weight percent and up to 100 weight percent (i.e., no solvent is added), up to 80 weight percent, or up to 60 weight percent. Suitable solvents are the same as those discussed above for reaction mixture 1A. The amount of solvent added is selected based on the desired viscosity, particularly the viscosity of the final polymerized material. The desired viscosity is usually sufficiently low so that the final polymeric material can be readily processed and/or applied to a substrate.

Reaction mixture 1C is exposed to actinic radiation (e.g., ultraviolet radiation) to commence controlled radical polymerization of monomer composition 1C. The resulting $P^3$ block or blocks can be a homopolymer or a random copolymer. Polymerization of monomer composition 1C can occur at room temperature (e.g., about 20° C. to 25° C.) but can also occur, if desired, at higher or lower temperatures.

Unless the polymeric material will be crosslinked with a crosslinking monomer having at least two ethylenically unsaturated groups, polymerization of reaction mixture 1C is usually allowed to proceed until greater than 80 weight percent, greater than 85 weight percent, greater than 90 weight percent, greater than 95 weight percent, greater than 98 weight percent, greater than 99 weight percent, or 100 weight percent of the monomers in monomer composition 1C have undergone controlled radical polymerization. Alternatively, unreacted monomers can be removed from the polymerized material. One of skill in the art is familiar with methods of separating the polymeric material from residual monomers.

If the polymeric material will be crosslinked with a crosslinking monomer having at least two ethylenically unsaturated groups, polymerization of reaction mixture 1C can be allowed to proceed to any desired extent until at least 5 weight percent of monomer composition 1C has undergone controlled radical polymerization. For example, the polymerization reaction can proceed until at least 10 weight percent, at least 20 weight percent, at least 30 weight percent, at least 40 weight percent and up to 100 weight percent, up to 99 weight percent, up to 98 weight percent, up to 95 weight percent, up to 90 weight percent, up to 85 weight percent, up to 80 weight percent, up to 70 weight percent, up to 60 weight percent, or up to 50 weight percent of monomer composition 1C has undergone controlled radical polymerization. The resulting polymeric material can be combined with a second monomer composition containing a crosslinking monomer having at least two ethylenically unsaturated groups to form the crosslinkable composition.

The composition of polymeric block $P^3$ is typically different than the composition of polymeric block $P^2$, the composition of polymeric block $P^2$ is typically different than the composition of polymeric block $P^1$, and the composition of polymeric block $P^3$ can be the same as or different than the composition of polymeric block $P^1$. In some embodiments, polymeric blocks $P^3$ and $P^2$ have different glass transition temperatures and polymeric blocks $P^2$ and $P^1$ have different glass transition temperatures, as measured by Differential Scanning Calorimetry. In some embodiments, the difference in the glass transition temperature between the polymeric blocks is at least 40° C., at least 50° C., at least 60° C., at least 70° C., at least 80° C., at least 90° C., or at least 100° C.

Additional polymeric blocks can be added to the polymeric material of Formula (II-3) to form polymeric materials of Formula (II) where the variable y is greater than 3. Each successive precursor polymeric material is added to another monomer composition to form another reaction mixture. The reaction mixture is exposed to actinic radiation such as ultraviolet radiation to form the polymeric material with two additional polymeric blocks as described above.

Adjacent polymeric blocks typically have different compositions, different glass transition temperatures, and different solubility parameters. Because of these differences, a phase separated morphology may result. This phase separation leads to physical crosslinking within the block copolymer and can, for example, increase the cohesive strength of the polymeric material even in the absence of chemical crosslinks.

The amount of the photoinitiator of Formula (I) included in the reaction mixture for any block impacts the weight average molecular weight of the resulting polymeric block. That is, the weight average molecular weight can be controlled based on the amount of photoinitiator added to the reaction mixture. The amount of photoinitiator is typically in a range of 0.001 to 15 weight percent based on the weight of the monomers in the reaction mixture. For comparable reaction conditions, increasing the amount of photoinitiator tends to decrease the weight average molecular weight (as well as the number average molecular weight). The amount of the photoinitiator is typically at least 0.001 weight percent, at least 0.005 weight percent, at least 0.01 weight percent, at least 0.02 weight percent, at least 0.03 weight percent, or at least 0.5 weight percent and can be up to 15 weight percent, up to 12 weight percent, up to 10 weight percent, up to 8 weight percent, up to 6 weight percent, up to 5 weight percent, up to 3 weight percent, up to 2 weight percent, or up to 1 weight percent. This amount of photoinitiator often results in the formation of polymeric blocks having a weight average molecular weight in a range of 1,000 to 3,000,000 Daltons or in the range of 1,000 to 1 million Daltons.

The reaction mixtures used to form the polymeric material of Formula (II) typically do not include a chain transfer agent (such as mercaptans and carbon tetrabromide). Chain transfer agents are not needed to control the molecular weight of the resulting polymeric material. Rather, the molecular weight can be varied and controlled through selection of the desired amount of the photoinitiator of Formula (I) and of the desired reaction temperature.

For crosslinking, the polymeric material of Formula (II) (e.g., the polymeric material of Formula (II-1), (II-2), or (II-3)) is combined with a second monomer composition to provide a crosslinkable composition. The second monomer composition contains a crosslinking monomer having at least two ethylenically unsaturated groups. Optionally, the second monomer composition can also include one or more monomers having a single ethylenically unsaturated group. The polymeric material can have any desired number of polymeric blocks.

The polymeric material of Formula (II) that is combined with the second monomer composition in the crosslinkable composition can have any desired extent of polymerization in the outer block (e.g., polymeric block $P^1$ in Formula (II-1), polymeric block $P^2$ in Formula (II-2), or polymeric block $P^3$ in Formula (III-3)). In some embodiments, the outer blocks are fully polymerized (e.g., the outer blocks are greater than 99 weight percent polymerized based on the weight of monomers used to form the outer block), nearly fully polymerized (e.g., the outer blocks are at least 80 to 99 weight percent polymerized based on the weight of the monomers used to form the outer blocks), or are partially polymerized (e.g., 5 to 80 weight percent polymerized based on the weight of the monomers used to form the outer blocks). Polymeric material of Formula (II) with partially polymerized outer blocks are referred to as "syrup polymers".

Syrup polymers often includes 5 to 80 weight percent polymeric material of Formula (II) and 20 to 95 weight percent monomer having a single ethylenically unsaturated group based on a total weight of polymerized (i.e., reacted monomers) and polymerizable material (i.e., unreacted monomers). In some embodiments, the syrup polymer contains 10 to 80 weight percent polymeric material of Formula (II) and 20 to 90 weight percent monomer having a single ethylenically unsaturated group, 10 to 70 weight percent polymeric material of Formula (II) and 30 to 90 weight percent monomer having a single ethylenically unsaturated group, 10 to 60 weight percent polymeric material of Formula (II) and 40 to 90 weight percent monomer having a single ethylenically unsaturated group, 10 to 50 weight percent polymeric material of Formula (II) and 50 to 90 weight percent monomer having a single ethylenically unsaturated group, 10 to 40 weight percent polymeric material of Formula (II) and 60 to 90 weight percent monomer having a single ethylenically unsaturated group, 20 to 50 weight percent polymeric material of Formula (II) and 50 to 80 weight percent monomer having a single ethylenically unsaturated group, or 20 to 40 weight percent polymeric material of Formula (II) and 60 to 80 weight percent monomer having a single ethylenically unsaturated group. The amounts are based on a total weight of polymerized and polymerizable material.

If a syrup polymer is used in the crosslinkable composition, the second monomer composition includes a crosslinking monomer plus any unreacted monomers (i.e., monomers having a single ethylenically unsaturated group) that were present when the polymer of Formula (II) was formed. Optionally, the second monomer composition can further include other monomers having a single ethylenically unsaturated group that were not present when the polymer of Formula (I) was formed.

Suitable crosslinking monomers often contain at least two (meth)acryloyl groups, which are often acryloyl groups. Exemplary crosslinking monomers with two (meth)acryloyl groups include 1,2-ethanediol diacrylate, 1,3-propanediol diacrylate, 1,3-butanediol diacrylate, 1,4-butanediol diacrylate, 1,6-hexanediol diacrylate (HDDA), 1,9-nonanediol diacrylate, 1,12-dodecanediol diacrylate, bisphenol A diacrylate, diethylene glycol diacrylate, triethylene glycol diacrylate, tetraethylene glycol diacrylate, tripropylene glycol diacrylate, polyethylene glycol diacrylate, polypropylene glycol diacrylate, polyethylene/polypropylene copolymer diacrylate, and neopentylglycol hydroxypivalate diacrylate modified caprolactone. Exemplary crosslinking monomers with three or four (meth)acryloyl groups include, but are not limited to, trimethylolpropane triacrylate (e.g., commercially available under the trade designation TMPTA-N from Surface Specialties, Smyrna, Ga. and under the trade designation SR-351 from Sartomer, Exton, Pa.), pentaerythritol triacrylate (e.g., commercially available under the trade designation SR-444 from Sartomer), tris(2-hydroxyethylisocyanurate) triacrylate (commercially available under the trade designation SR-368 from Sartomer), pentaerythritol tetraacrylate (e.g., commercially available under the trade designation SR-295 from Sartomer), di-trimethylolpropane tetraacrylate (e.g., commercially available under the trade designation SR-355 from Sartomer), and ethoxylated pentaerythritol tetraacrylate (e.g., commercially available under the trade designation SR-494 from Sartomer). An exemplary crosslinking monomer with five (meth)acryloyl groups includes, but is not limited to, dipentaerythritol pentaacrylate (e.g., commercially available under the trade designation SR-399 from Sartomer).

Regardless of whether the polymeric material of Formula (II) is a syrup polymer, a nearly fully polymerized polymeric material, or a fully polymerized polymeric material, the crosslinkable composition usually includes 0.01 to 20 weight percent crosslinking monomer based on a total weight of polymerized and polymerizable material. In many embodiments, the crosslinkable composition contains at least 0.05 weight percent, at least 0.1 weight percent, at least 0.5 weight percent, or at least 1 weight percent and up to 15 weight percent, up to 10 weight percent, up to 5 weight percent, up to 2 weight percent, or up to 1 weight percent crosslinking monomer based on the total weight of polymerized and polymerizable material. Any other monomers included in the crosslinkable composition have a single ethylenically unsaturated group.

Thus, the overall crosslinkable composition contains 5 to 99.99 weight percent polymeric material of Formula (II) and a second monomer composition containing 1) 0.01 to 20 weight percent crosslinking monomer having at least two ethylenically unsaturated groups and 2) 0 to 95 weight percent monomer having a single ethylenically unsaturated group. In some embodiments, the crosslinkable composition contains 10 to 99.99 weight percent polymeric material of Formula (II) and a second monomer composition containing 1) 0.01 to 10 weight percent crosslinking monomer having at least two ethylenically unsaturated groups and 2) 0 to 90 weight percent (0 to 89.99 weight percent) monomers having a single ethylenically unsaturated group. In other embodiments, the crosslinkable composition contains 10 to 80 weight percent polymeric material of Formula (II) and a second monomer composition containing 1) 0.01 to 10 weight percent crosslinking monomer having at least two ethylenically unsaturated groups and 2) 10 to 90 weight percent monomers (10 to 89.99 weight percent) having a single ethylenically unsaturated group. In still other embodiments, the crosslinkable composition contains 10 to 60 weight percent polymeric material of Formula (II) and a second monomer composition containing 1) 0.01 to 10 weight percent crosslinking monomer having at least two ethylenically unsaturated groups and 2) 30 to 90 weight percent (30 to 89.99 weight percent) monomers having a single ethylenically unsaturated group. In yet other embodiments, the crosslinkable composition contains 10 to 40 weight percent polymeric material of Formula (II) and a second monomer composition containing 1) 0.01 to 10 weight percent crosslinking monomer having at least two ethylenically unsaturated groups and 2) 50 to 90 weight percent (50 to 89.99 weight percent) monomers having a single ethylenically unsaturated group. The amounts are based on a total weight of polymerized and polymerizable material in the crosslinkable composition. In a still further embodiment, the crosslinkable composition contains 10 to 40 weight percent polymeric material of Formula (II) and a second monomer composition containing 1) 0.01 to 5 weight percent crosslinking monomer having at least two ethylenically unsaturated groups and 2) 55 to 90 weight percent (55 to 89.99 weight percent) monomers having a single ethylenically unsaturated group. The amounts are based on a total weight of polymerized and polymerizable material.

In some specific embodiments, the polymeric material of Formula (II) is selected so that the final crosslinked composition is suitable for use as a pressure-sensitive adhesive composition. Although the polymeric material included in a pressure-sensitive adhesive can have multiple polymeric blocks, the polymeric material often contains a single polymeric block. That is, the variable y in Formula (II) is equal to 1, which is equivalent to the polymeric material of Formula (II-1).

For use as a pressure-sensitive adhesive, the monomers selected to form the polymeric material of Formula (II) are those that will result in an elastomeric material. The elastomeric material typically has a glass transition temperature (Tg) that is no greater than 20° C., no greater than 10° C., no greater than 0° C., no greater than −10° C., no greater than −20° C., no greater than −30° C., no greater than −40° C., or no greater than −50° C. The glass transition temperature can be measured using techniques such as Differential Scanning Calorimetry and Dynamic Mechanical Analysis. Alternatively, the glass transition temperature can be estimated using the Fox equation. Lists of glass transition temperatures for homopolymers are available from multiple monomer suppliers such as from BASF Corporation (Houston, Tex., USA), Polysciences, Inc. (Warrington, Pa., USA), and Aldrich (Saint Louis, Mo., USA) as well as in various publications such as, for example, Mattioni et al., *J. Chem. Inf. Comput. Sci.*, 2002, 42, 232-240.

To form an elastomeric polymeric material of Formula (II-1), monomeric composition 1A, which is herein also referred to as the first monomer composition, often contains at least one low Tg monomer. As used herein, the term "low Tg monomer" refers to a monomer having a Tg no greater than 20° C. when homopolymerized (i.e., a homopolymer formed from the low Tg monomer has a Tg no greater than 20° C.). Suitable low Tg monomers are often selected from an alkyl (meth)acrylates, heteroalkyl (meth)acrylates, aryl substituted alkyl acrylate, and aryloxy substituted alkyl acrylates.

Example low Tg alkyl (meth)acrylate monomers often are non-tertiary alkyl acrylates but can be alkyl methacrylates having a linear alkyl group with at least 4 carbon atoms. Specific examples of alkyl (meth)acrylates include, but are not limited to, n-butyl acrylate, n-butyl methacrylate, isobutyl acrylate, sec-butyl acrylate, n-pentyl acrylate, 2-methylbutyl acrylate, n-hexyl acrylate, cyclohexyl acrylate, 4-methyl-2-pentyl acrylate, 2-methylhexyl acrylate, 2-ethylhexyl acrylate, n-octyl acrylate, 2-octyl acrylate, isooctyl acrylate, isononyl acrylate, isoamyl acrylate, n-decyl acrylate, isodecyl acrylate, n-decyl methacrylate, lauryl acrylate, isotridecyl acrylate, n-octadecyl acrylate, isostearyl acrylate, n-dodecyl methacrylate, an isomer of any of these monomers, or mixtures of multiple isomers.

Example low Tg heteroalkyl (meth)acrylate monomers often have a heteroalkyl group at least 3 carbon atoms, at least 4 carbon atoms, or at least 6 carbon atoms and can have up to 30 or more carbon atoms, up to 20 carbon atoms, up to 18 carbon atoms, up to 16 carbon atoms, up to 12 carbon atoms, or up to 10 carbon atoms. Specific examples of heteroalkyl (meth)acrylates include, but are not limited to, 2-ethoxyethyl acrylate, 2-(2-ethoxyethoxy)ethyl acrylate, 2-methoxyethyl (meth)acrylate, and tetrahydrofurfuryl (meth)acrylate.

Exemplary aryl substituted alkyl acrylates or aryloxy substituted alkyl acrylates include, but are not limited to, 2-biphenylhexyl acrylate, benzyl acrylate, 2-phenoxyethyl acrylate, and 2-phenylethyl acrylate.

Monomer composition 1A (i.e., first monomer composition) used in reaction mixture 1A, which is herein also referred to as the "first reaction mixture", for forming a polymeric material of Formula (II) often contains at least 40 weight percent of a low Tg monomer based on a total weight of monomers in monomer composition 1A. In some embodiments, monomer composition 1A contains at least 45 weight percent, at least 50 weight percent, at least 60 weight percent, at least 65 weight percent, at least 70 weight percent, at least 75 weight percent, or at least 80 weight percent and up to 100 weight percent, up to 99 weight percent, up to 98 weight percent, up to 95 weight percent, up to 90 weight percent, or up to 85 weight percent of the low Tg monomer.

Some monomer compositions 1A can include an optional polar monomer. The polar monomer has an ethylenically unsaturated group plus a polar group such as an acidic group or a salt thereof, a hydroxyl group, a primary amido group, a secondary amido group, a tertiary amido group, or an amino group. Having a polar monomer often facilitates adherence of the pressure-sensitive adhesive to a variety of substrates.

Exemplary polar monomers with an acidic group include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinyl phosphonic acid, and mixtures thereof Due to their availability, the acid monomers are often (meth)acrylic acids.

Exemplary polar monomers with a hydroxyl group include, but are not limited to, hydroxyalkyl (meth)acrylates (e.g., 2-hydroxyethyl (meth)acrylate, 2-hydroxypropyl (meth)acrylate, 3-hydroxypropyl (meth)acrylate, and 4-hydroxybutyl (meth)acrylate), hydroxyalkyl (meth)acrylamides (e.g., 2-hydroxyethyl (meth)acrylamide or 3-hydroxypropyl (meth)acrylamide), ethoxylated hydroxyethyl (meth) acrylate (e.g., monomers commercially available from Sartomer (Exton, Pa., USA) under the trade designation CD570, CD571, and CD572), and aryloxy substituted hydroxyalkyl (meth)acrylates (e.g., 2-hydroxy-2-phenoxypropyl (meth)acrylate).

Exemplary polar monomers with a primary amido group include (meth)acrylamide. Exemplary polar monomers with secondary amido groups include, but are not limited to, N-alkyl (meth)acrylamides such as N-methyl (meth)acrylamide, N-ethyl (meth)acrylamide, N-isopropyl (meth)acrylamide, N-tert-octyl (meth)acrylamide, or N-octyl (meth) acrylamide.

Exemplary polar monomers with a tertiary amido group include, but are not limited to, N-vinyl caprolactam, N-vinyl-2-pyrrolidone, (meth)acryloyl morpholine, and N,N-dialkyl (meth)acrylamides such as N,N-dimethyl (meth)acrylamide, N,N-diethyl (meth)acrylamide, N,N-dipropyl (meth)acrylamide, and N,N-dibutyl (meth)acrylamide.

Polar monomers with an amino group include various N,N-dialkylaminoalkyl (meth)acrylates and N,N-dialkylaminoalkyl (meth)acrylamides. Examples include, but are not limited to, N,N-dimethyl aminoethyl (meth)acrylate, N,N-dimethylaminoethyl (meth)acrylamide, N,N-dimethylaminopropyl (meth)acrylate, N,N-dimethylaminopropyl (meth)acrylamide, N,N-diethylaminoethyl (meth)acrylate, N,N-diethylaminoethyl (meth)acrylamide, N,N-diethylaminopropyl (meth)acrylate, and N,N-diethylaminopropyl (meth)acrylamide.

The amount of the optional polar monomer is often in a range of 0 to 30 weight percent based on the weight of monomers in monomer composition 1A (i.e., first monomer composition). If present, the amount of polar monomers in the first monomer composition is often at least 0.1 weight percent, at least 0.5 weight percent, or at least 1 weight percent based on the total weight of monomers in monomer composition 1A. The amount can be up to 30 weight percent, up to 25 weight percent, up to 20 weight percent, up to 15 weight percent, up to 10 weight percent, or up to 5 weight percent. For example, the amount is often in a range of 0 to 30 weight percent, in a range of 0 to 20 weight percent, in a range of 0 to 15 weight percent, in a range of 0 to 10 weight percent, in a range of 0 to 5 weight percent, in a range of 0.5 to 15 weight percent, in a range of 1 to 15 weight percent, or in a range of 1 to 10 weight percent based on a total weight of monomers in monomer composition 1A.

Monomer composition 1A (i.e., first monomer composition) can optionally include a high Tg monomer. As used herein, the term "high Tg monomer" refers to a monomer that has a Tg greater than 30° C., greater than 40° C., or greater than 50° C. when homopolymerized (i.e., a homopolymer formed from the monomer has a Tg greater than 30° C., greater than 40° C., or greater than 50° C.). Some suitable high $T_g$ monomers have a single (meth)acryloyl group such as, for example, methyl methacrylate, ethyl methacrylate, n-propyl methacrylate, isopropyl methacrylate, n-butyl methacrylate, isobutyl methacrylate, sec-butyl methacrylate, tert-butyl (meth)acrylate, cyclohexyl methacrylate, isobornyl (meth)acrylate, stearyl (meth)acrylate, phenyl acrylate, benzyl methacrylate, 3,3,5 trimethylcyclohexyl (meth)acrylate, 2-phenoxyethyl methacrylate, N-octyl (meth)acrylamide, and mixtures thereof While various vinyl monomers that do not have a (meth)acryloyl group also are classified as high Tg monomers, they are listed separately below.

The amount of high Tg monomer used to form the polymeric material of Formula (II) can be up to 50 weight percent or even higher provided that the Tg of the polymeric material is no greater than 20° C. In some embodiments, the amount can be up to 40 weight percent, up to 30 weight percent, up to 20 weight percent, up to 15 weight percent, or up to 10 weight percent. The amount can be at least 1 weight percent, at least 2 weight percent, or at least 5 weight percent. For example, the amount can be in a range of 0 to 50 weight percent, 0 to 40 weight percent, 0 to 30 weight percent, 0 to 20 weight percent, 0 to 10 weight percent, 1 to 30 weight percent, 1 to 20 weight percent, or 1 to 10 weight percent. The amount values are based on a total weight of monomers in monomer composition 1A (i.e., first monomer composition).

Still further, monomer composition 1A (i.e., first monomer composition) can optionally include a vinyl monomer (i.e., a monomer with an ethylenically unsaturated group that is not a (meth)acryloyl group). Examples of optional vinyl monomers include, but are not limited to, various vinyl ethers (e.g., vinyl methyl ether), vinyl esters (e.g., vinyl acetate and vinyl propionate), styrene, substituted styrene (e.g., a-methyl styrene), vinyl halide, and mixtures thereof The vinyl monomers having a group characteristic of polar monomers are considered herein to be polar monomers. The vinyl monomers often have a high Tg such as the (meth)acryloyl-containing high Tg monomers described above.

The amount of the optional vinyl monomer lacking a (meth)acryloyl group is often in a range of 0 to 15 weight percent based on the weight of monomers in monomer composition 1A (i.e., the first monomer composition). If present, the amount of vinyl monomers in the first monomer composition is often at least 0.1 weight percent, 0.2 weight percent, 0.5 weight percent, or 1 weight percent based on the total weight of monomers in the first monomer composition. The amount can be up to 15 weight percent, up to 10 weight percent, or up to 5 weight percent. For example, the amount is often in a range of 0 to 15 weight percent, in a range of 0.1 to 10 weight percent, in a range of 0.5 to 5 weight percent, or in a range of 1 to 5 weight percent based on a total weight of monomers in the first monomer composition.

Overall, the elastomeric polymeric material of Formula (II-1) can be formed from a first monomer composition that includes up to 100 weight percent of the low Tg monomer. In some embodiments, the first monomer composition contains 100 weight percent low Tg monomer based on the total weight of monomers in the first monomer composition. In other embodiments, the first monomer composition contains 40 to 100 weight percent of the low Tg monomer, 0 to 30 weight percent polar monomer, 0 to 50 weight percent high Tg monomer, and 0 to 15 weight percent vinyl monomers not having a (meth)acryloyl group. In still other embodiments, the first monomer composition contains 60 to 100 weight percent of the low Tg monomer, 0 to 20 weight percent polar monomer, 0 to 40 weight percent high Tg monomer, and 0 to 10 weight percent vinyl monomers not having a (meth)acryloyl group. In yet other embodiments, the first monomer composition contains 75 to 100 weight percent of the low Tg monomer, 0 to 10 weight percent polar monomer, 0 to 25 weight percent high Tg monomer, and 0 to 5 weight percent vinyl monomers not having a (meth) acryloyl group.

The resulting elastomeric polymeric material of Formula (II-1) contains up to 100 weight percent or 100 weight percent low Tg monomer units. The weight percent value is based on the total weight of monomeric units in the polymeric material. In some embodiments, the polymeric material contains 40 to 100 weight percent of the low Tg monomeric units, 0 to 15 weight percent polar monomeric units, 0 to 50 weight percent high Tg monomeric units, and 0 to 15 weight percent vinyl monomeric units. In still other embodiments, the polymer contains 60 to 100 weight percent of the low Tg monomeric units, 0 to 10 weight percent polar monomeric units, 0 to 40 weight percent high Tg monomeric units, and 0 to 10 weight percent vinyl monomeric units. In yet other embodiments, the polymer contains 75 to 100 weight percent of the low Tg monomeric units, 0 to 10 weight percent polar monomeric units, 0 to 25 weight percent high Tg monomeric units, and 0 to 5 weight percent monomeric units.

The weight average molecular weight of the elastomeric polymeric material of Formula (II-1) is often in a range of 10,000 Da to 1,000,000 Da or even higher. For example, the weight average molecular weight can be at least 20,000 Da, at least 30,000 Da, at least 40,000 Da, or at least 50,000 and can be up to 1,000,000 Da, up to 900,000 Da, up to 800,000 Da, up to 700,000 Da, or up to 600,000 Da.

The elastomeric material of Formula (II-1) can be a fully polymerized polymeric material (e.g., the outer blocks are greater than 99 weight percent polymerized based on the weight of monomers used to form polymeric block $P^1$), a nearly fully polymerized (e.g., the outer blocks are at least 80 to 99 weight percent polymerized polymeric material based on the weight of the monomers used to form polymeric block $P^1$), or are partially polymerized (e.g., 5 to 80 weight percent polymerized polymeric material based on the weight of the monomers used to form polymeric block $P^1$). The partially polymerized polymeric materials are syrup polymers.

Using a syrup polymer rather than a fully or nearly fully polymerized polymeric material can be advantageous in some embodiments. The photoinitiators of Formula (I) allow the formation of syrup polymers that include polymeric chains with a narrower distribution of molecular weights compared to conventionally prepared syrup polymers. These conventionally prepared syrup polymers often contain a small number of longer chains resulting in syrups with higher viscosities. That is, the viscosity of the syrup polymer can be more easily controlled and adjusted with polymeric materials formed using the photoinitiators of Formula (I).

The elastomeric material of Formula (II-1) is combined with a second monomer composition containing a crosslinking monomer having at least two ethylenically unsaturated groups. In some embodiments, the only monomer in the second monomer composition is the crosslinking monomer. In other embodiments, the second monomer composition further includes a monomer having a single ethylenically unsaturated group. The single ethylenically unsaturated monomer can be a residual monomer remaining in the syrup polymer or can be additional monomers that were not included in the monomer composition used to form the elastomeric material of Formula (II-1). Examples of additional monomers are any of those described above.

In addition to the polymeric material of Formula (II) (including elastomeric material of Formula (II-1)) and the various monomers, the crosslinkable composition can optionally further include a photoinitiator. The initiator can be a photoinitiator of Formula (I), a photoinitiator not of Formula (I) such as a conventionally used photoinitiator for free radical polymerization reactions, or mixtures thereof. Suitable photoinitiator compounds that are not of Formula (I) include, for example, benzoin ethers (e.g., benzoin methyl ether or benzoin isopropyl ether) or substituted benzoin ethers (e.g., anisoin ether). Other exemplary photoinitiators are substituted acetophenones such as 2,2-diethoxyacetophenone or 2,2-dimethoxy-2-phenylacetophenone (commercially available under the trade designation OMNIRAD 651 from IGM Resins (Saint Charles, Ill., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(O-ethoxycarbonyl) oxime. Other suitable photoinitiators include, for example, 1-hydroxycyclohexyl phenyl ketone (commercially available under the trade designation OMNIRAD 184), bis(acyl) phenyl phosphine oxides such as bis(2,4,6-trimethylbenzoyl)phenyl phosphine oxide (commercially available under the trade designation OMNIRAD 819), 1-[4-(2-hydroxyethoxy)phenyl]-2-hydroxy-2-methyl-1-propane-1-one (commercially available under the trade designation OMNIRAD 2959), 2-benzyl-2-dimethylamino-1-(4-morpholinophenyl)butanone (commercially available under the trade designation OMNIRAD 369), 2-methyl-1-[4-(methylthio) phenyl]-2-morpholinopropan-1-one (commercially available under the trade designation OMNIRAD 907), and 2-hydroxy-2-methyl-1-phenyl propan-1-one (commercially available under the trade designation OMNIRAD 1173 from IGM Resins (Saint Charles, Ill., USA)). In some embodiments, the photoinitiator is a substituted acetophenone or a bis(acyl)phenyl phosphine oxide.

The amount of any added photoinitiator is often in a range of 0 to 1 weight percent based on a total weight of polymerized and polymerizable material. For example, the amount can be at least 0.01 weight percent, at least 0.02 weight percent, at least 0.05 weight percent, or at least 0.1 weight percent and can be up to 1 weight percent, up to 0.8 weight percent, up to 0.5 weight percent, or up to 0.3 weight percent.

An organic solvent can be added, if desired, to control the viscosity of the crosslinkable composition. In many embodiments, no organic solvent (i.e., the curable composition is free of organic solvent) or only a minimum amount of the organic solvent is added. The amount of organic solvent can be up to 60 weight percent or even higher based on a total weight of the crosslinkable composition. The amount of organic solvent can be up to 50 weight percent, up to 40 weight percent, up to 30 weight percent, up to 20 weight percent, up to 10 weight percent, or up to 5 weight percent. In some embodiments, it is desirable to keep the content of organic solvent as low as possible. Any organic solvent used in the second reaction mixture is typically removed at the completion of the crosslinking reaction. Suitable organic solvents include, but are not limited to, methanol, tetrahydrofuran, ethanol, isopropanol, heptane, acetone, methyl ethyl ketone, methyl acetate, ethyl acetate, toluene, xylene, and ethylene glycol alkyl ether. Those solvents can be used alone or as mixtures thereof.

To form a crosslinked composition, the crosslinkable composition is often applied as a layer to a substrate and then exposed to actinic radiation (e.g., ultraviolet radiation). Any suitable substrate can be used. Stated differently, an article is provided that includes a first substrate and a crosslinkable composition layer positioned adjacent the first substrate. Any of the crosslinkable composition described above can be used in the crosslinkable composition layer.

The crosslinkable composition layer can be positioned adjacent to the substrate using any suitable process such as, for example, flow coating, dip coating, spray coating, knife coating, die coating, or extrusion. Once positioned adjacent to the substrate, the crosslinkable coating layer is exposed to actinic radiation (e.g., ultraviolet radiation) to react the second monomer composition and form the crosslinkable composition.

The use of polymeric material of Formula (II) in the crosslinkable composition is particularly advantageous due to its active end groups (terminal groups). As with the formation of each block of the polymeric material of Formula (II), upon exposure of the crosslinkable composition to actinic radiation (e.g., ultraviolet radiation), photolysis occurs releasing the radical of formula $R^1$—(CS)—S*. Monomers in the crosslinkable composition can polymerize to form crosslinked polymeric block attached to each of the outer blocks in the polymeric material of Formula (II). The product is a crosslinked polymeric material.

If polymeric materials are formed using conventional methods using that lack active terminal groups (such as $R^1$—(CS)—S— groups in the polymeric materials of Formula (II)) are combined with a crosslinking monomer having multiple ethylenically unsaturated groups, a second polymeric material forms that is separate from the original polymeric material. The second polymeric material is crosslinked in the presence of the original polymeric material and the result is the formation of a gelled network. The original polymeric material is not involved in the crosslinking reaction and usually is not covalently attached to the second polymeric material in the gelled network.

In contrast, the polymeric material of Formula (II) has terminal $R^1$—(CS)—S— groups. When exposed to actinic radiation (e.g., ultraviolet radiation), radicals of formula $R^1$—(CS)—S* are released and the original polymeric material undergoes chain extension and crosslinking reactions. There is no additional second polymeric material formed that is separate from the original polymeric material. That is, the original polymeric material itself is involved in the crosslinking reaction.

The crosslinkable composition can be exposed to actinic radiation (e.g., ultraviolet radiation) having a UVA maximum in a range of 280 to 450 nanometers. Ultraviolet light sources can be of various types. Low light intensity lights such as black lights, generally provide intensities ranging from 0.1 or 0.5 mW/cm$^2$(milliWatts per square centimeter) to 10 mW/cm$^2$ (as measured in accordance with procedures approved by the United States National Institute of Standards and Technology as, for example, with a UVIMAP UM 365 L-S radiometer manufactured by Electronic Instrumentation & Technology, Inc., (Sterling, Va.)). High light intensity sources generally provide intensities greater than 10, 15, or 20 mW/cm$^2$ ranging up to 450 mW/cm$^2$ or greater. In some embodiments, high intensity light sources provide intensities up to 500, 600, 700, 800, 900 or 1000 mW/cm$^2$. UV light to polymerize the monomer component(s) can be provided by various light sources such as light emitting diodes (LEDs), black lights, medium pressure mercury lamps, etc., or a combination thereof The monomer component(s) can also be polymerized with higher intensity light sources, as available from Fusion UV Systems Inc. The UV exposure time for polymerization and curing can vary depending on the intensity of the light source(s) used. For example, complete curing with a low intensity light course can be accomplished with an exposure time ranging from about 30 to 300 seconds; whereas complete curing with a high intensity light source can be accomplished with shorter exposure time ranging from about 5 to 20 seconds. Partial curing with a high intensity light source can typically be accomplished with exposure times ranging from about 2 seconds to about 5 or 10 seconds.

In some embodiments, it is preferable to use lights that emit a narrow spectrum of light in the ultraviolet region of the electromagnetic spectrum. These light sources, which can include LEDs and lasers, can result in the formation of crosslinkable compositions without the need to add conventional photoinitiators prior to the curing process. These light sources can enhance the rate of polymerization while maintaining the reactive nature of the polymeric material.

In other embodiments, where broader wavelength ultraviolet light sources are used such as black lights, conventional photoinitiators may need to be added to the crosslinkable compositions prior to crosslinking.

The polymeric materials of Formula (I) have dithiocarbamate or dithiocarbonate terminal groups. That is, the terminal group is typically $R^1$—(CS)—S—. Further, some of the crosslinked polymeric materials may have these terminal groups. If desired, this terminal group can be replaced after the polymeric material has formed using known methods such as those described, for example, in (a) Taton et al., *Handbook of RAFT Polymerization*, Barner-Kowollik, ed., Wiley-VCH: Weinheim, Germany, 2008, p. 373, (b) Destarac et al., Polym. Prepr. (Am. Chem. Soc., Div. Polym. Chem.), 2008, 49 (2), (c) Destarac, Polymer Preprints, 2008, 49 (2), page 179, and (d) Tsarevsky et al., in *Controlled Radical Polymerization: Mechanisms*, ACS Symposium Series, American Chemical Society, Washington, D.C., 2015, 211-246. Suitable methods include, for example, converting the dithiocarbamate or dithiocarbonate functionality into a thiol end group through reaction with nucleophiles. The polymeric material with the thiol end group can undergo various radical reactions (e.g., radical catalyzed thiol-ene reactions and radical catalyzed thiol-yne reactions), nucleophilic reactions (e.g., thiol-ene Michael addition reactions, thiol-epoxy reactions, thiol-halide reactions, thiol-isocyanate reactions), or sulfur exchange reactions (e.g., thiol-alkanethiosulfonate reactions and thiol-pyridyl disulfide reactions). Other example methods include free-radical reductive cleavage of the dithiocarbamate or dithiocarbonate groups, oxidation with peroxide and ozone, and aminolysis using an amine or ammonia.

Either the polymeric material of Formula (II) or a crosslinkable composition that contains the polymeric material of Formula (II) can be positioned on any suitable substrate to provide an article. The substrate can be flexible or inflexible and can be formed from a polymeric material, glass or ceramic material, metal, or a combination thereof. Some substrates are polymeric films such as those prepared from polyolefins (e.g., polyethylene, polypropylene, or copolymers thereof), polyurethanes, polyvinyl acetates, polyvinyl chlorides, polyesters (polyethylene terephthalate or polyethylene naphthalate), polycarbonates, polymethyl(meth)acrylates (PMMA), ethylene-vinyl acetate copolymers, and cellulosic materials (e.g., cellulose acetate, cellulose triacetate, and ethyl cellulose). Other substrates are metal foils, non-woven materials (e.g., paper, cloth, nonwoven scrims), foams (e.g., polyacrylic, polyethylene, polyurethane, neoprene), and the like. For some substrates, it may be desirable to treat the surface to improve adhesion to the polymeric material and/or to the crosslinkable composition and/or to the crosslinked composition. Such treatments include, for example, application of primer layers, surface modification layer (e.g., corona treatment or surface abrasion), or both.

In some embodiments, the substrate is a release liner. Release liners typically have low affinity for the polymeric material, crosslinkable composition, and crosslinked composition. Exemplary release liners can be prepared from paper (e.g., Kraft paper) or other types of polymeric material. Some release liners are coated with an outer layer of a release agent such as a silicone-containing material or a fluorocarbon-containing material.

The polymeric material or the crosslinkable composition can be positioned next to a substrate using a roll-to-roll process. That is, the substrate can be moved from a first roll to a second roll in a continuous process. As the substrate moves between the first roll and the second roll, it can be coated with the polymeric material or with the crosslinkable composition. Such a substrate can be regarded as being a web and the web is often a polymeric material such as those described above. The polymeric web can be unrolled from a first roll, coated with the crosslinkable composition, exposed to actinic radiation (e.g., ultraviolet radiation) for crosslinking, and then rolled onto the second roll.

The polymeric material or the crosslinkable composition coating can have any desired thickness. The thickness of the crosslinkable composition coating is typically selected so that it can be effectively crosslinked when exposed to actinic radiation (e.g., ultraviolet radiation). In many embodiments, the crosslinkable composition coating has a thickness no greater than 20 mils (500 micrometers), no greater than 10 mils (250 micrometers), no greater than 5 mils (125 micrometers), no greater than 4 mils (100 micrometers), no greater than 3 mils (75 micrometers), or no greater than 2 mils (50 micrometers). The thickness is often at least 0.5 mils (12.5 micrometers) or at least 1 mil (25 micrometers). For example, the thickness of the crosslinkable composition coating can be in the range of 0.5 mils (2.5 micrometers) to 20 mils (500 micrometers), in the range of 0.5 mils (5 micrometers) to 10 mils (250 micrometers), in the range of 0.5 mils (12.5 micrometers) to 5 mils (125 micrometers), in the range of 1 mil (25 micrometers) to 3 mils (75 micrometers), or in the range of 1 mil (25 micrometers) to 2 mils (50 micrometers).

In some embodiments, the crosslinked composition is a pressure-sensitive adhesive. Thus, articles with a layer of the crosslinked composition have a pressure-sensitive adhesive layer and can be used for many applications typical of such articles. The substrate adjacent to the pressure-sensitive layer can be selected depending on the specific application. For example, the substrate can be a sheeting material and the resulting article can provide decorative graphics or can be a reflective product. In other examples, the substrate can be label stock (the resulting article is a label with an adhesive layer), a tape backing (the resulting article is an adhesive tape), or a foam. In yet other examples, the substrate can be a release liner and the resulting article can be a transfer tape. The transfer tape can be used to transfer the pressure-sensitive adhesive layer to another substrate or surface. Other substrates and surface include, for example, a panel (e.g., a metal panel such as an automotive panel) or a glass window.

Some articles are adhesive tapes. The adhesive tapes can be single-sided adhesive tapes with the crosslinkable composition attached to a single side of the tape backing or can be double-sided adhesive tape with a pressure-sensitive adhesive layer on both major surfaces of the tape backing. At least one of the two pressure-sensitive adhesive layers is the crosslinkable composition described above. Double-sided adhesive tapes are often carried on a release liner.

If desired, tackifiers can be added to the crosslinkable composition used to form pressure-sensitive adhesives compositions. Suitable tackifying resins include rosin resins such as rosin acids and their derivatives (e.g., rosin esters); terpene resins such as polyterpenes (e.g., alpha pinene-based resins, beta pinene-based resins, and limonene-based resins) and aromatic-modified polyterpene resins (e.g., phenol modified polyterpene resins); coumarone-indene resins; and petroleum-based hydrocarbon resins such as C5-based hydrocarbon resins, C9-based hydrocarbon resins, C5/C9-based hydrocarbon resins, and dicyclopentadiene-based resins. These tackifying resins, if added, can be hydrogenated to lower their color contribution to the pressure-sensitive adhesive composition. Combinations of various tackifiers can be used, if desired.

Various embodiments are provided that are reaction mixtures, polymeric materials, crosslinkable compositions, crosslinked compositions, articles containing the polymeric materials, articles containing the crosslinkable compositions or the crosslinked compositions, methods of making articles, and photoinitiators are provided.

Embodiment 1A is a polymeric material of Formula (II).

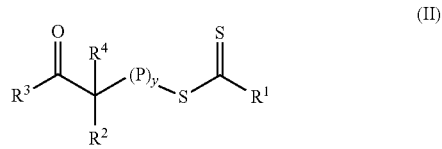

(II)

In Formula (II), group $R^1$ is an alkoxy, aralkyloxy, alkenoxy or $-N(R^5)_2$. Groups $R^2$ and $R^3$ are each independently an alkyl, aryl, aralkyl, alkaryl, or a group of formula $-R^6-(OR^6)_n-OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. Each P is a polymeric block that comprises a polymerized product of a first monomer composition comprising at least one monomer having a single ethylenically unsaturated group and y is an integer in a range of 1 to 10.

Embodiment 2A is the polymeric material of embodiment 1A, wherein the polymeric material of Formula (II) is of Formula (II-A).

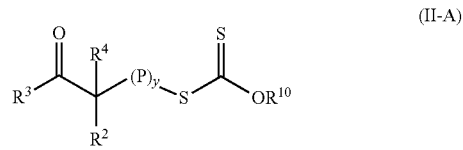

(II-A)

In Formula (II-A), $-OR^{10}$ is an alkoxy, aralkyloxy, alkenoxy (i.e., $R^{10}$ is alkyl, aralkyl, or alkenyl).

Embodiment 3A is the polymeric material of embodiment 2A, wherein $-OR^{10}$ is an alkoxy.

Embodiment 4A is the polymeric material of embodiment 1A, wherein the polymeric material of Formula (II) is of Formula (II-B).

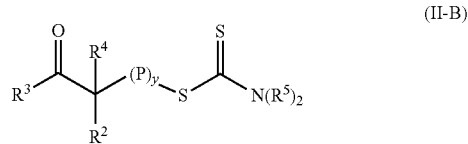

(II-B)

Embodiment 5A is the polymeric material of embodiment 4A, wherein each $R^5$ is an alkyl.

Embodiment 6A is any one of embodiments 1A to 5A, wherein y is equal to 1 (there is one polymeric block) and the polymeric material is of Formula (II-1).

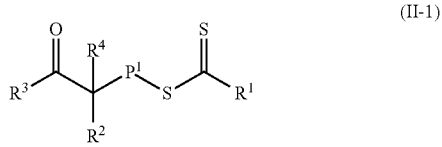

In Formula (II-1), $P^1$ is a first polymeric block.

Embodiment 7A is any one of embodiments 1A to 5A, wherein y is equal to 2 (there are two polymeric blocks) and the polymeric material is of Formula (II-2).

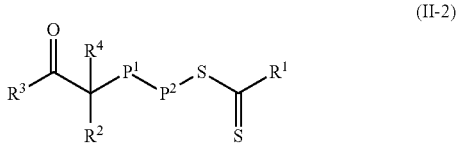

Embodiment 8A is the polymeric material of embodiment 7A, wherein $P^2$ has monomeric units different than $P^1$.

Embodiment 9A is the polymeric material of any one of embodiments 1A to 5A, wherein y is equal to 3 (there are three polymeric blocks) and the polymeric material is of Formula (III-3).

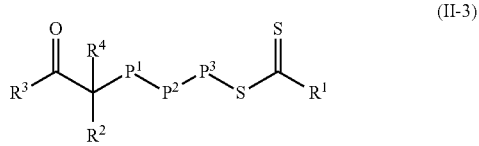

Embodiment 10A is the polymeric material of embodiment 9A, wherein $P^3$ has monomeric units different than $P^2$ and wherein $P^2$ has monomeric units different than $P^1$.

Embodiment 11A is the polymeric material of any one of embodiments 1A to 10A, wherein the polymeric material is an elastomeric material.

Embodiment 12A is the polymeric material of embodiment 11A, wherein the elastomeric material has a glass transition temperature (Tg) no greater than 20° C. when measured using Differential Scanning Calorimetry.

Embodiment 13A is the polymeric material of any one of embodiments 1A to 12A, wherein $R^4$ is hydrogen.

Embodiment 14A is the polymeric material of any one of embodiments 1A to 13A, wherein $R^2$ is alkyl.

Embodiment 1B is a first reaction mixture. The reaction mixture contains a) a photoinitiator of Formula (I)

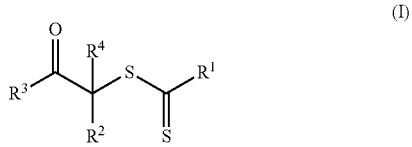

and b) a monomer composition 1A comprising at least one monomer having a single ethylenically unsaturated group, wherein the molar ratio of the first monomer to the photoinitiator is at least 3:1. In Formula (I), group $R^1$ is an alkoxy, aralkyloxy, alkenoxy or —$N(R^5)_2$. Groups $R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero.

Embodiment 2B is the first reaction mixture of embodiment 1B, wherein the photoinitiator of Formula (I) is of Formula (I-A)

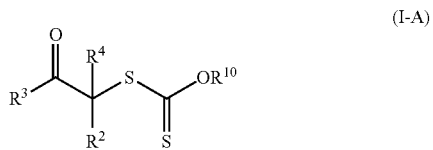

In Formula (I-A), —$OR^{10}$ is an alkyloxy, aralkyloxy, or alkenoxy (i.e., $R^{10}$ is an alkyl, aralkyl, or alkenyl).

Embodiment 3B is the first reaction mixture of embodiment 2B, wherein —$OR^{10}$ is an alkoxy.

Embodiment 4B is the first reaction mixture of any one of embodiments 1B to 3B, wherein $R^4$ is hydrogen.

Embodiment 5B is the first reaction mixture of embodiment 1B, wherein the photoinitiator of Formula (I) is of Formula (I-B).

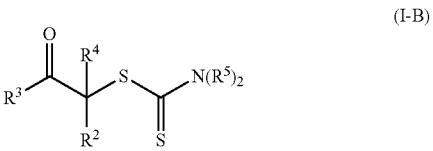

Embodiment 6B is the first reaction mixture of embodiment 5B, wherein each $R^5$ is an alkyl.

Embodiment 7B is the first reaction mixture of embodiment 6B, wherein $R^4$ is hydrogen.

Embodiment 8B is the first reaction mixture of any one of embodiments 1B to 7B, wherein the monomer composition 1A comprises 50 to 100 weight percent of a first monomer with a single (meth)acryloyl group and 0 to 50 weight percent of a second monomer having a single ethylenically unsaturated group that is not a (meth)acryloyl group. The weight percent is based on the total weight of monomers in the monomer composition 1A.

Embodiment 9B is the first reaction mixture of any one of embodiments 1B to 8B, wherein the first reaction mixture is free of a monomer having more than one ethylenically unsaturated group.

Embodiment 1C is a second reaction mixture. The second reaction mixture includes a) a polymeric material of Formula (II-1)

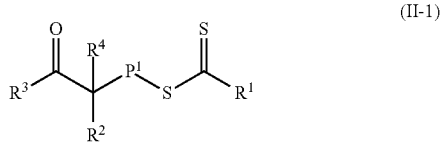

(II-1)

and b) a monomer composition 1B. In Formula (II-1), group $R^1$ is an alkoxy, aralkyloxy, alkenoxy or —$N(R^5)_2$. Groups $R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. $P^1$ is a first polymeric block that is a polymerized product of a monomer composition 1A having at least one monomer having a single ethylenically unsaturated group. Monomer composition 1B comprises at least one monomer having a single ethylenically unsaturated group, wherein monomer composition 1B is different than monomer composition 1A used to form $P^1$.

Embodiment 2C is the second reaction mixture of embodiment 1C, wherein the monomer composition 1B comprises 50 to 100 weight percent of a first monomer with a single (meth)acryloyl group and 0 to 50 weight percent of a second monomer having a single ethylenically unsaturated group that is not a (meth)acryloyl group. The weight percent is based on the total weight of monomers in the monomer composition 1B.

Embodiment 3C is the second reaction mixture of embodiment 1C or 2C, wherein the second reaction mixture is free of a monomer having more than one ethylenically unsaturated group.

Embodiment 1D is a third reaction mixture. The second reaction mixture includes a) a polymeric material of Formula (II-2)

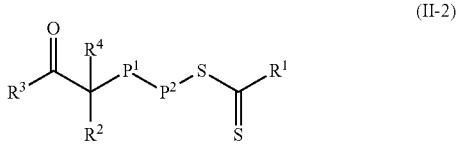

(II-2)

and b) a monomer composition 1C. In Formula (II-2), group $R^1$ is an alkoxy, aralkyloxy, alkenoxy or —$N(R^5)_2$. Groups $R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group. Group is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. $P^1$ is a first polymeric block that is a polymerized product of a monomer composition 1A having at least one monomer having a single ethylenically unsaturated group. $P^2$ is a second polymeric block that is a polymerized product of a monomer composition 1B having at least one monomer having a single ethylenically unsaturated group, wherein monomer composition 1B is different than monomer composition 1A used to form $P^1$. Monomer composition 1C comprises at least one monomer having a single ethylenically unsaturated group, wherein monomer composition 1C is different than monomer composition 1B used to form $P^2$.

Embodiment 2D is the third reaction mixture of embodiment 1D, wherein the monomer composition 1B comprises 50 to 100 weight percent of a first monomer with a single (meth)acryloyl group and 0 to 50 weight percent of a second monomer having a single ethylenically unsaturated group that is not a (meth)acryloyl group. The weight percent is based on the total weight of monomers in the monomer composition 1C.

Embodiment 3D is the third reaction mixture of embodiment 1D or 2D, wherein the third reaction mixture is free of a monomer having more than one ethylenically unsaturated group.

Embodiment 1E is a crosslinkable composition. The crosslinkable composition contains a) a polymeric material of Formula (II)

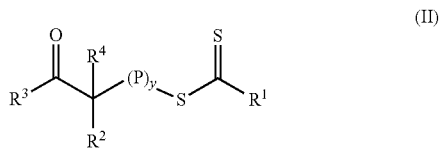

(II)

and b) a second monomer composition comprising a crosslinking monomer having at least two ethylenically unsaturated groups. In Formula (II), group $R^1$ is an alkoxy, aralkyloxy, alkenoxy or —$N(R^5)$2. Groups $R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. Each P is a polymeric block that comprises a polymerized product of a first monomer composition comprising at least one monomer having a single ethylenically unsaturated group and y is an integer in a range of 1 to 10.

Embodiment 2E is the crosslinkable composition of embodiment 1E, wherein the polymeric material of Formula (II) is of any one of embodiments 2A to 13A.

Embodiment 3E is the crosslinkable composition of embodiment 1E or 2E, wherein the polymeric material of Formula (II) (such as Formula (II-1)) is an elastomeric material.

Embodiment 4E is the crosslinkable composition of any one of embodiments 1E to 3E, wherein the second monomer composition further comprises a monomer having a single ethylenically unsaturated group.

Embodiment 5E is the crosslinkable composition of any one of embodiments 1E to 4E, wherein the crosslinkable composition comprises 1) 5 to 99.99 weight percent polymeric material of Formula (II) and 2) a second monomer composition comprising a) 0.01 to 20 weight percent crosslinking monomer having at least two ethylenically unsaturated groups, and b) 0 to 95 weight percent monomer having a single ethylenically unsaturated group, wherein each amount is based on a total weight of polymerized and polymerizable material.

Embodiment 6E is the crosslinkable composition of any one of embodiments 1E to 5E, wherein the crosslinkable composition comprises 1) 10 to 60 weight percent polymeric material of Formula (II) and 2) a second monomer composition comprising a) 0.01 to 10 weight percent crosslinking monomer having at least two ethylenically unsaturated groups, and b) 30 to 90 weight percent monomer having a single ethylenically unsaturated group, wherein each amount is based on a total weight of polymerized and polymerizable material.

Embodiment 7E is the crosslinkable composition of any one of embodiments 1E to 6E, wherein the crosslinkable composition comprises 1) 10 to 40 weight percent polymeric material of Formula (II) and 2) a second monomer composition comprising a) 0.01 to 5 weight percent crosslinking monomer having at least two ethylenically unsaturated groups, and b) 55 to 90 weight percent monomer having a single ethylenically unsaturated group, wherein each amount is based on a total weight of polymerized and polymerizable material.

Embodiment 8E is the crosslinkable composition of any one of embodiments 1E to 7E, wherein the polymeric material of Formula (II) is of Formula (II-1)

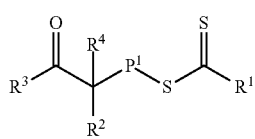
(II-1)

and is a reaction product of first monomer composition comprising 40 to 100 weight percent of a low Tg monomeric unit, 0 to 15 weight percent of a polar monomeric unit, 0 to 50 weight percent of a high Tg monomeric unit (i.e., a high Tg (meth)acryloyl-containing monomeric unit), and 0 to 15 weight percent vinyl monomeric units based on a total weight of monomeric units.

Embodiment 9E is the crosslinkable composition of any one of embodiments 1E to 8E, wherein the polymeric material of Formula (II) has a weight average molecular weight in a range of 10,000 Daltons to 5 million Daltons.

Embodiment 10E is the crosslinkable composition of any one of embodiments 1E to 9E, wherein the crosslinkable composition further comprises a photoinitiator.

Embodiment 11E is the crosslinkable composition of embodiment 10E, wherein the photoinitiator is of Formula (I).

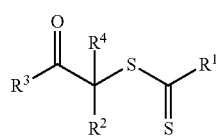
(I)

In Formula (I), group $R^1$, $R^2$, and $R^3$ are the same as in Formula (II).

Embodiment 12E is the crosslinkable composition of embodiment 10E, wherein the photoinitiator is not of Formula (I).

Embodiment 13E is the crosslinkable composition of any one of embodiments 1E to 12E, wherein the crosslinkable composition further comprises a tackifier.

Embodiment 1F is a crosslinked composition that includes a cured product of a crosslinkable composition. The crosslinkable composition is according to embodiment 1E.

Embodiment 2F is the crosslinked composition of embodiment 1F, wherein the crosslinkable composition is according to any one of embodiments 2E to 13E.

Embodiment 3F is the crosslinked composition of embodiment 1F or 2F, wherein the crosslinked composition is a pressure-sensitive adhesive.

Embodiment 1G is an article that includes a first substrate and a crosslinkable composition layer adjacent to the substrate, wherein the crosslinkable composition is of embodiment 1E.

Embodiment 2G is the article of embodiment 1G, wherein the crosslinkable composition is according to any one of embodiments 2E to 13E.

Embodiment 1H is an article that includes a first substrate and a crosslinked composition layer adjacent to the substrate, wherein the crosslinked composition layer includes a cured product of a crosslinkable composition of embodiment 1E.

Embodiment 2H is the article of embodiment 1H, wherein the crosslinkable composition is according to any one of embodiments 2E to 13E.

Embodiment 1J is an article that includes a first substrate and a polymeric material adjacent to the substrate, wherein the polymeric material is of embodiment 1A.

Embodiment 2J is the article of embodiment 1J, wherein the polymeric material is of any one of embodiments 2A to 13A.

Embodiment 1K is a method of making an article. The method includes providing a first substrate and applying a layer of a crosslinkable composition adjacent to the first substrate. The crosslinkable composition is of embodiment 1E. The method further includes exposing the layer of crosslinkable composition to actinic radiation to form a layer of crosslinked composition. The actinic radiation includes actinic radiation.

Embodiment 2K is the method of embodiment 1K, wherein the crosslinkable composition is of embodiment 2E to 13E.

Embodiment 3K is the method of embodiment 1K or 2K, wherein the substrate is in the form of a polymeric web.

Embodiment 4K is the method of embodiment on any one of embodiments 1K to 3K, wherein the actinic radiation is from a light emitting diode.

Embodiment 1L is a method of making a polymeric material. The method includes providing a photoinitiator of Formula (I).

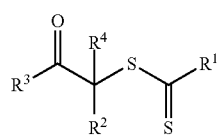
(I)

In Formula (I), group $R^1$ is an alkoxy, aralkyloxy, alkenoxy or $-N(R^5)_2$. Groups $R^2$ and $R^3$ are each independently an alkyl, aryl, aralkyl, alkaryl, or a group of formula $-R^6-(OR^6)_n-OR^7$, or $R^2$ and $R^3$ combine to form a ring structure containing the carbonyl group. Group $R^4$ is an alkyl or hydrogen. Each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic. Each $R^6$ is an alkylene, group $R^7$ is an alkyl, and n is an integer greater than or equal to zero. The method further includes preparing a first reaction mixture comprising the photoinitiator of Formula (I) and a first monomer composition 1A comprising at least one monomer having a single ethylenically unsaturated group. The method still further includes forming a first polymeric material of Formula (II-1) from the first reaction mixture.

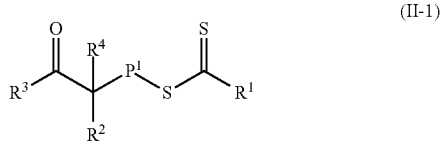
(II-1)

$P^1$ is a first polymeric block that is a polymerized product of a monomer composition 1A having at least one monomer having a single ethylenically unsaturated group.

EXAMPLES

Test Methods

Peel Adhesion Strength

Stainless steel (SS) panels were cleaned by wiping them three times using methyl ethyl ketone and a clean lint-free tissue. The cleaned panels were allowed to dry at room temperature. Tape samples measuring 0.5 inch (1.27 centimeters) wide and 8 inches (20.3 centimeters) long were cut, then centered on the cleaned panels and adhered to one end such that tape overlapped the panel by 25.4 millimeters (1 inch) in the lengthwise direction. The tape sample was then rolled down one time in each direction using a 4.5 pound (ca. 2 kilograms) rubber roller. After conditioning for 15 minutes at 23° C. (73° F.) and 50% relative humidity (RH), the peel adhesion strength was measured, under the same temperature and relative humidity as used above, at an angle of 180 degrees and a rate of 305 millimeters/minute (12 inches/minute) using a peel adhesion tester (IMASS Slip/Peel Tester, Model SP-2000, available from IMASS Incorporated, Accord, Mass.). Four samples were evaluated, the results normalized to ounces/inch (oz/in) and the average value calculated. The results were reported in both ounces/inch (oz/in) and Newtons/decimeter (N/dm).

Shear Adhesion Strength—Elevated Temperature

Stainless steel (SS) panels were cleaned by wiping them three times using methyl ethyl ketone and a clean lint-free tissue. Tape samples measuring 0.5 inch (1.27 centimeters) wide and between 3 and 4 inches (7.6 and 10.2 centimeters) long were cut, then centered on the cleaned panels and adhered to one end such that tape overlapped the panel by 25.4 millimeters (1 inch) in the lengthwise direction. The tape sample was then rolled down one time in each direction using a 4.5 pound (ca. 2 kilograms) rubber roller. After conditioning the tape/test panel assembly for 15 minutes at 23° C. (73° F.), it was suspended in a stand in an oven heated to 158° F. (70° C.) and tilted at an angle of 2° from vertical to ensure a shear force. A 500 gram weight was hung from the free end of the tape sample. The time, in minutes, for the tape to fall from the panel was recorded. The test was terminated if failure had not occurred in 10,000 minutes and the result recorded as "10,000+". One test sample was run for each tape construction.

Molecular Weight by Gel Permeation Chromatography (GPC)

Molecular weights and polydispersity were determined at 35° C. by gel permeation chromatography (GPC) using a Waters LC SYSTEM (Waters Corporation, Milford, Mass.) equipped with a Waters STYRAGEL HR 5E THF 300 millimeter (length)×7.8 millimeter I.D. (Inside Diameter) column, in combination with a Waters 2414 REFRACTIVE INDEX DETECTOR. Sample solutions were prepared by adding 10 milliliters of tetrahydrofuran (THF) to a sample weighing between approximately 50 and 100 milligrams, and mixing for at least one hour followed by filtering through a 0.2 micrometer polytetrafluoroethylene syringe filter. The injection volume was 20 microliters and the THF eluent flow rate was 1.0 milliliter/minute. Weight and Number Average Molecular Weights (Mw and Mn, grams/mole) and polydispersity index, PDI (Mw/Mn) were determined relative to a calibration curve with polystyrene standards.

NMR Analysis

Approximately 50-100 milligrams of the polymer reaction were dissolved in approximately 1 milliliter of deuterated chloroform and NMR spectra were acquired on a Bruker AVANCE III 500 MHz spectrometer equipped with a broadband cryoprobe. Spectra were acquired with a low tip angle(15°) and a relaxation delay of 4 seconds for good quantitation. Two dimensional (2D) NMR experiments (gCOSY, TOCSY, gHSQC, and gHMBC) were run to assign the free initiator and different polymer end groups. Peak assignments for the different polymeric chains are given in the examples section for each unique initiator. The peak assignments were confirmed from a 2D gHMBC experiment, which provides the highest level of structural detail. A variety of parameters were determined from the integrals in the NMR spectra, including percent conversion, the number average molecular weight (Mn) of the polymeric material, and the mole fraction of free initiator remaining. Percent conversion was calculated as the moles of polymer repeat units (integral of resonance at 4.03 ppm divided by 2 for poly(BA)) divided by the sum of moles of polymer repeat units and moles of unreacted monomer (integral of resonance at 6.40 ppm). The degree of polymerization (DP) was determined from the moles of polymer repeat unit divided by the moles of polymer chains. From the calculated DP, the Mn is calculated as DP*128.17 for poly(BA) (the molecular weight of a BA repeat unit is 128.17 grams/mole). The mole fraction of free initiator remaining was calculated from the moles of free initiator divided by the moles of total initiator species (moles of free initiator plus moles of polymer chains). The moles of polymer chains are determined from the photoinitiator related polymer end groups (most typically $R^3$ in Formula (II)).

Sodium Isopropyl Xanthate

In a flask equipped with a mechanical stirrer, isopropanol (871.10 grams, 14.49 moles) was bubbled with nitrogen. Sodium metal cubes (20.25 grams, 0.88 moles, Sigma-Aldrich Corporation, Milwaukee, Wis.) were cut into small pieces and added to the flask over 3 hours. The temperature was then increased to 65° C. The sodium dissolved with evolution of hydrogen over 3 additional hours resulting in a clear solution. The mixture was cooled to 35° C. using an ice bath, which resulted in a thick slurry. Carbon disulfide (73.80 grams, 0.97 moles) was then added slowly over 30 minutes. After full addition, the mixture was stirred for an additional 30 minutes resulting in a yellow solution. Solvent was removed by placing the mixture under vacuum resulting in a yellow solid. The product was further dried under high vacuum (1 millimeter Hg) for 4 hours resulting in a yellow powder (136.67 grams).

Preparation of
O-Isopropyl-S-acetonyl-dithiocarbonate (PI-1)

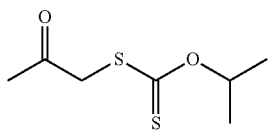

A mixture of sodium isopropyl xanthate (5.00 grams, 32 millimoles) and acetone (35 milliliters) was cooled using an ice bath. A solution of 1-chloropropan-2-one (2.59 grams, 28 millimoles, TCI America, Portland, OR) in acetone (5 milliliters) was added slowly over 5 minutes. After stirring at room temperature for 2 hours, the solvent was removed under vacuum. Ethyl acetate (30 milliliters) was added and the mixture was washed once with water. The organic phase was concentrated under vacuum and the residual oil was purified by column chromatography over silica gel (2 to 20% ethyl acetate in hexanes). A yellow oil was isolated (4.95 grams).

Preparation of O-Ethyl-S-phenacyl dithiocarbonate (PI-2)

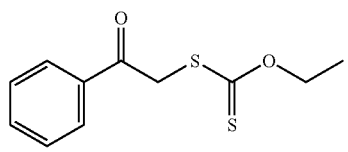

A mixture of potassium ethyl xanthate (6.22 grams, 39 millimoles, Alfa Aesar, Ward Hill, Mass.) and acetone (30 milliliters) was cooled using an ice bath. A solution of 2-chloro-1-phenyl-ethanone (5.00 grams, 32 millimoles, TCI America) in acetone (15 milliliters) was added slowly over 15 minutes. After stirring at room temperature for 1 hour, the solvent was removed under vacuum. Ethyl acetate (60 milliliters) was added and the mixture was washed with water two times. The organic phase was concentrated under vacuum and the residual oil was purified by column chromatography over silica gel (1 to 15% ethyl acetate in hexanes). A slightly yellow solid was isolated (6.04 grams).

Preparation of Carboonodithioic Acid O-isopropyl S-(3-pentane-2-4-dione) ester (PI-3)

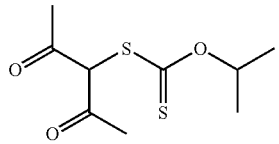

A mixture of sodium isopropyl xanthate (4.23 grams, 27 millimoles) and acetone (50 milliliters) was cooled using an ice bath. A solution of 3-chloropentane-2,4-dione (3.00 grams, 22 millimoles) in acetone (5 milliliters) was added slowly over 5 minutes. After stirring at room temperature for 3 hours, the solvent was removed under vacuum. Ethyl acetate (30 milliliters) was added and the mixture was washed once with water. The organic phase was concentrated under vacuum and the residual oil was purified by column chromatography over silica gel (1 to 10% ethyl acetate in hexanes). A yellow solid was isolated (4.30 grams).

Preparation of Carbonodithioic Acid O-(isopropyl) S-(1-methyl-2-oxopropyl) ester (PI-4)

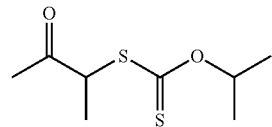

A mixture of sodium isopropyl xanthate (4.90 grams, 31 millimoles) and acetone (40 milliliters) was cooled using an ice bath. A solution of 3-chloro-2-butanone (3.00 grams, 28 millimoles, TCI America) in acetone (5 milliliters) was added slowly over 5 minutes. After stirring at room temperature for 2 hours, the solvent was removed under vacuum. Ethyl acetate (100 milliliters) was added and the mixture was washed once with water. The organic phase was concentrated under vacuum and the residual oil was purified by column chromatography over silica gel (1 to 18% ethyl acetate in hexanes). A yellow oil was isolated (5.02 grams).

Preparation of Carbonodithioic Acid O-(isopropyl) S-(1,1-dimethyl-2-oxopropyl) ester (PI-5)

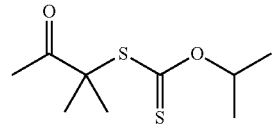

A mixture of sodium isopropyl xanthate (3.16 grams, 20 millimoles) and acetone (35 milliliters) was cooled using an ice bath. A solution of 3-bromo-3-methyl-2-butanone (3.00 grams, 18 millimoles, TCI America) in acetone (5 milliliters) was added slowly over 5 minutes. After stirring at room temperature for 3 hours, the solvent was removed under vacuum. Ethyl acetate (50 milliliters) was added and the mixture was washed once with water. The organic phase was concentrated under vacuum and the residual oil was purified by column chromatography over silica gel (2 to 15% ethyl acetate in hexanes). A yellow oil was isolated (3.56 grams).

Preparation of Carbonodithioic Acid O-(isopropyl) S-(1-methoxy-2-oxopropyl) ester PI-6)

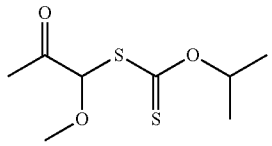

A mixture of pyruvic aldehyde dimethyl acetal (25.00 grams, 212 millimoles, Sigma-Aldrich, Milwaukee, Wis.), acetyl chloride (30.2 milliliters, 425 millimoles, Alfa Aesar), and iodine (0.10 grams) was heated at 50° C. for 17 hours. After cooling to room temperature, the reaction mixture was distilled at atmospheric pressure to remove excess acetyl chloride (distilled at 52° C.). The residue was cooled to room temperature and further distilled at 45-51° C. and 0.6 millimeters Hg to give an orange liquid (1-chloro-1-methoxy-propan-2-one, 13.11 grams).

A mixture of sodium isopropyl xanthate (4.26 grams, 27 millimoles) and acetone (60 milliliters) was cooled using an ice bath. A solution of 1-chloro-1-methoxy-propan-2-one (3.00 grams, 24 millimoles) in acetone (10 milliliters) was added slowly over 5 minutes. After stirring at room temperature for 17 hours, the solvent was removed under vacuum. Ethyl acetate (50 milliliters) was added and the mixture was washed once with water. The organic phase was concentrated under vacuum and the residual oil was purified by column chromatography over silica gel (2 to 20% ethyl acetate in hexanes). A yellow oil was isolated (4.68 grams).

Preparation of Carbonodithioic Acid O-isopropyl S-(1-methyl-2-oxo-2-phenylethyl) ester (PI-7)

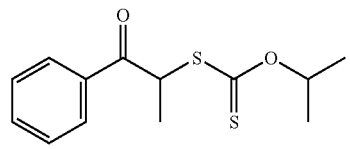 [SMILES: CC(C)OC(=S)SC(C)C(=O)c1ccccc1]

A mixture of sodium isopropyl xanthate (3.27 grams, 21 millimoles) and acetone (40 milliliters) was cooled using an ice bath. A solution of 2-bromo-1-phenyl-propan-1-one (4.00 grams, 19 millimoles, TCI America) in acetone (5 milliliters) was added slowly over 5 minutes. After stirring at room temperature for 17 hours, the solvent was removed under vacuum. Ethyl acetate (50 milliliters) was added and the mixture was washed once with water. The organic phase was concentrated under vacuum and the residual oil was purified by column chromatography over silica gel (3 to 20% ethyl acetate in hexanes). A yellow oil was isolated (3.37 grams).

Preparation of Carbonodithioic Acid S-(1-phenyl-2-oxo-2-phenylethyl) ester (PI-8)

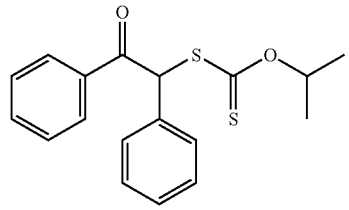 [SMILES: CC(C)OC(=S)SC(C(=O)c1ccccc1)c1ccccc1]

A mixture of sodium isopropyl xanthate (3.77 grams, 24 millimoles) and acetone (50 milliliters) was cooled using an ice bath. A solution of desyl chloride (5.00 grams, 22 millimoles, Sigma Aldrich) in acetone (5 milliliters) was added slowly over 5 minutes. After stirring at room temperature for 2 hours, the solvent was removed under vacuum. Ethyl acetate (100 milliliters) was added and the mixture was washed once with water. The organic phase was concentrated under vacuum and the residual oil was purified by column chromatography over silica gel (ethyl acetate). A yellow solid was isolated (3.84 grams).

Preparation of Carbonodithioic Acid N-diethyl S-(1-methyl-2-oxo-2-phenylethyl) ester (PI-9)

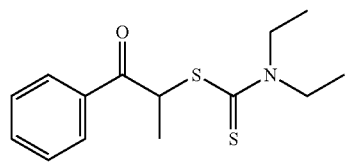 [SMILES: CCN(CC)C(=S)SC(C)C(=O)c1ccccc1]

A mixture of diethyl dithiocarbamate trihydrate (3.49 grams, 16 millimoles) and acetone (40 milliliters) was cooled using an ice bath. A solution of 2-bromo-1-phenyl-propan-1-one (3.00 grams, 14 millimoles, TCI America) in acetone (5 milliliters) was added slowly over 5 minutes. After stirring at room temperature for 4 hours, the solvent was removed under vacuum. Ethyl acetate (50 milliliters) was added and the mixture was washed once with water. The organic phase was concentrated under vacuum and the residual oil was purified by column chromatography over silica gel (5 to 25% ethyl acetate in hexanes). A slightly yellow solid was isolated (3.61 grams).

Preparation of Polymers

Examples 1-6 and Comparative Examples 1-3

Polymers of 2-ethylhexyl acrylate were prepared using Photoinitiators 1-6 (PI 1-6) using the materials and amounts shown in Table 1 below. A solution of 2-ethylhexyl acrylate (2EHA, available from BASF Corporation, Charlotte, N.C.), photoinitiator, and ethyl acetate was placed in a 250 milliliter, 2-necked round bottom flask and degassed with a nitrogen stream for 15 minutes. The flask was then held under a positive pressure of nitrogen, stirred magnetically, and irradiated with light emitting diodes (LED) using a 365 nanometer LED array (Model LED365-0556 LED Bank, Clearstone Technologies, Incorporated, Hopkins, Minn.) at a power setting of 15% and a distance of 3 inches from the flask edge. The total energy provided after an exposure time of 5 minutes was 1850 milliJoules/square centimeters at the surface of the flask. Samples were removed at intervals throughout the polymerization and molecular weights were determined by gel permeation chromatography (GPC). Monomer conversion (mole %) was determined from NMR analysis using the following procedure. 2EHA conversion was calculated as the amount of poly(2EHA) (integral of resonance at 3.94 ppm divided by 2) divided by the sum of poly(2EHA) and unreacted monomer 2EHA (integral of resonance at 5.80 ppm) multiplied by 100. The results are shown in Tables 2-10.

TABLE 1

Compositions

| Example | Photoinitiator | Photoinitiator (grams) | 2EHA (grams) | Ethyl acetate (grams) |
|---|---|---|---|---|
| C1 | PI-1 | 0.150 | 25.033 | 25.095 |
| C2 | PI-2 | 0.109 | 25.141 | 25.035 |
| C3 | PI-3 | 0.108 | 25.005 | 25.040 |
| 1 | PI-4 | 0.140 | 25.012 | 25.015 |
| 2 | PI-5 | 0.104 | 25.005 | 25.310 |
| 3 | PI-6 | 0.118 | 25.028 | 25.055 |
| 4 | PI-7 | 0.142 | 25.033 | 25.045 |
| 5 | PI-8 | 0.108 | 25.085 | 25.021 |
| 6 | PI-9 | 0.133 | 25.020 | 25.143 |

C: Comparative Example

TABLE 2

Results for 2EHA and PI-1

| Example | Irradiation Time (minutes) | 2EHA Conversion (mole %) | Mn (grams/ mole) | Mw (grams/ mole) | PDI |
|---|---|---|---|---|---|
| C1-1 | 1.0 | 15.0 | 252,500 | 400,000 | 1.58 |
| C1-2 | 2.0 | 26.5 | 207,400 | 351,500 | 1.69 |
| C1-3 | 3.5 | 36.6 | 169,700 | 311,700 | 1.84 |
| C1-4 | 6.0 | 53.4 | 148,000 | 270,300 | 1.83 |
| C1-5 | 8.5 | 63.1 | 131,100 | 256,200 | 1.95 |
| C1-6 | 13.5 | 74.9 | 112,900 | 245,100 | 2.17 |
| C1-7 | 21.0 | 83.3 | 91,700 | 219,000 | 2.39 |
| C1-8 | 29.5 | 88.5 | 83,900 | 219,400 | 2.62 |

C: Comparative Example

TABLE 3

Results for 2EHA and PI-2

| Example | Irradiation Time (minutes) | 2EHA Conversion (mole %) | Mn (grams/ mole) | Mw (grams/ mole) | PDI |
|---|---|---|---|---|---|
| C2-1 | 1.0 | 19.0 | 96,500 | 156,500 | 1.62 |
| C2-2 | 2.0 | 33.6 | 81,600 | 139,000 | 1.70 |
| C2-3 | 3.0 | 44.7 | 72,300 | 131,700 | 1.82 |
| C2-4 | 4.0 | 53.6 | 66,300 | 125,200 | 1.89 |
| C2-5 | 6.5 | 66.1 | 61,700 | 120,400 | 1.95 |
| C2-6 | 9.0 | 74.4 | 60,000 | 119,900 | 2.00 |
| C2-7 | 16.0 | 84.4 | 55,100 | 115,800 | 2.10 |
| C2-8 | 34.5 | 92.0 | 50,100 | 111,900 | 2.23 |

C: Comparative Example

TABLE 4

Results for 2EHA and PI-3

| Example | Irradiation Time (minutes) | 2EHA Conversion (mole %) | Mn (grams/ mole) | Mw (grams/ mole) | PDI |
|---|---|---|---|---|---|
| C3-1 | 7.5 | 14.8 | 523,300 | 844,700 | 1.61 |
| C3-2 | 16.5 | 26.6 | 458,400 | 812,100 | 1.77 |
| C3-3 | 29.5 | 39.0 | 496,200 | 942,800 | 1.90 |
| C3-4 | 53.5 | 58.8 | 403,300 | 763,000 | 1.89 |

C: Comparative Example

TABLE 5

Results for 2EHA and PI-4

| Example | Irradiation Time (minutes) | 2EHA Conversion (mole %) | Mn (grams/ mole) | Mw (grams/ mole) | PDI |
|---|---|---|---|---|---|
| 1-1 | 1.5 | 20.9 | 14,900 | 26,500 | 1.78 |
| 1-2 | 2.5 | 37.1 | 16,900 | 31,900 | 1.89 |
| 1-3 | 3.0 | 42.1 | 17,700 | 33,500 | 1.89 |
| 1-4 | 5.0 | 56.4 | 19,600 | 37,400 | 1.91 |
| 1-5 | 6.5 | 64.7 | 21,600 | 40,700 | 1.88 |
| 1-6 | 9.0 | 72.1 | 22,400 | 41,400 | 1.85 |
| 1-7 | 13.0 | 81.0 | 24,500 | 44,200 | 1.80 |
| 1-8 | 24.5 | 89.2 | 25,900 | 45,800 | 1.77 |

TABLE 6

Results for 2EHA and PI-5

| Example | Irradiation Time (minutes) | 2EHA Conversion (mole %) | Mn (grams/ mole) | Mw (grams/ mole) | PDI |
|---|---|---|---|---|---|
| 2-1 | 3.0 | 15.5 | 11,000 | 19,300 | 1.75 |
| 2-2 | 5.0 | 28.3 | 15,900 | 34,800 | 2.19 |
| 2-3 | 6.5 | 39.3 | 22,200 | 51,400 | 2.32 |
| 2-4 | 8.0 | 52.3 | 25,800 | 62,200 | 2.41 |
| 2-5 | 11.0 | 66.1 | 32,300 | 72,600 | 2.25 |
| 2-6 | 14.5 | 76.0 | 34,800 | 74,300 | 2.14 |
| 2-7 | 21.0 | 83.1 | 37,800 | 76,700 | 2.03 |
| 2-8 | 29.5 | 88.1 | 40,100 | 77,700 | 1.94 |

TABLE 7

Results for 2EHA and PI-6

| Example | Irradiation Time (minutes) | 2EHA Conversion (mole %) | Mn (grams/ mole) | Mw (grams/ mole) | PDI |
|---|---|---|---|---|---|
| 3-1 | 4.5 | 11.1 | 9,700 | 16,100 | 1.66 |
| 3-2 | 8.5 | 24.9 | 12,900 | 26,500 | 2.05 |
| 3-3 | 11.0 | 37.5 | 18,000 | 40,200 | 2.23 |
| 3-4 | 14.0 | 55.5 | 25,500 | 58,900 | 2.31 |
| 3-5 | 16.5 | 65.1 | 29,700 | 64,300 | 2.16 |
| 3-6 | 19.5 | 74.1 | 32,700 | 68,200 | 2.09 |
| 3-7 | 25.5 | 83.0 | 35,200 | 70,100 | 1.99 |
| 3-8 | 33.5 | 87.9 | 35,600 | 70,500 | 1.98 |

TABLE 8

Results for 2EHA and PI-7

| Example | Irradiation Time (minutes) | 2EHA Conversion (mole %) | Mn (grams/mole) | Mw (grams/mole) | PDI |
|---|---|---|---|---|---|
| 4-1 | 1.0 | 14.4 | 15,300 | 27,700 | 1.81 |
| 4-2 | 2.0 | 25.8 | 17,100 | 32,500 | 1.90 |
| 4-3 | 3.0 | 36.0 | 18,800 | 3,6900 | 1.96 |
| 4-4 | 5.5 | 55.6 | 24,100 | 47,200 | 1.96 |
| 4-5 | 7.5 | 64.2 | 27,000 | 51,600 | 1.91 |
| 4-6 | 11.0 | 73.8 | 29,100 | 54,900 | 1.89 |
| 4-7 | 17.5 | 83.1 | 31,600 | 57,700 | 1.83 |
| 4-8 | 39.0 | 91.5 | 33,400 | 59,400 | 1.78 |

TABLE 9

Results for 2EHA and PI-8

| Example | Irradiation Time (minutes) | 2EHA Conversion (mole %) | Mn (grams/mole) | Mw (grams/mole) | PDI |
|---|---|---|---|---|---|
| 5-1 | 7.5 | 13.4 | 25,200 | 44,300 | 1.76 |
| 5-2 | 15.0 | 27.4 | 34,200 | 64,100 | 1.87 |
| 5-3 | 19.5 | 39.8 | 43,100 | 83,500 | 1.94 |
| 5-4 | 25.0 | 56.3 | 51,900 | 106,400 | 2.05 |
| 5-5 | 29.5 | 66.6 | 59,400 | 117,800 | 1.98 |
| 5-6 | 35.0 | 75.7 | 65,100 | 128,500 | 1.97 |
| 5-7 | 45.0 | 84.2 | 67,000 | 132,200 | 1.97 |
| 5-8 | 56.5 | 88.5 | 68,400 | 133,700 | 1.95 |

In example 6, the flask was irradiated with light emitting diodes (LED) using a 365 nanometer LED array (Model LED365-0556 LED Bank, Clearstone Technologies, Incorporated, Hopkins, Minn.) at a power setting of 100% and a distance of 3 inches from the flask edge. The total energy provided after an exposure time of 1 minute was 3081 milliJoules/square centimeters at the surface of the solution.

TABLE 10

Results for 2EHA and PI-9

| Example | Irradiation Time (minutes) | 2EHA Conversion (mole %) | Mn (grams/mole) | Mw (grams/mole) | PDI |
|---|---|---|---|---|---|
| 6-1 | 0.5 | 10.4 | 34,300 | 68,400 | 1.99 |
| 6-2 | 1.0 | 16.7 | 30,900 | 62,700 | 2.03 |
| 6-3 | 2.0 | 26.9 | 25,800 | 59,800 | 2.32 |
| 6-4 | 5.0 | 40.8 | 26,500 | 57,600 | 2.17 |
| 6-5 | 12.0 | 55.8 | 26,100 | 59,000 | 2.26 |
| 6-6 | 20.5 | 65.0 | 30,200 | 61,800 | 2.05 |
| 6-7 | 44.5 | 77.3 | 33,100 | 67,900 | 2.05 |

Example 7 and Comparative Example 4

Copolymers of the 2EHA polymers Comparative Example 2-8 and Example 4-8, prepared as described above, and isobutyl acrylate (IBA) were prepared as follows. Isobutyl acrylate (2.50 grams, IBA, Alfa Aesar) and ethyl acetate (2.50 grams) were added to the final poly(2EHA) solution from Comparative Example 2 (C2-8) and Example 4 (4-8) (5.00 grams of each solution) in vials. The solutions were purged with dry nitrogen for 10 minutes and the vials capped. The vials were then placed on a roller and irradiated with light emitting diodes (LED) using a 365 nanometer LED array (Model LED365-0556 LED Bank, Clearstone Technologies, Incorporated) at a power setting of 15% and a distance of 3 inches from the top of the vials. The total energy provided after an exposure time of 1 minute was 793 milliJoules/square centimeters at the top of the vial. After a total of 45 minutes of LED exposure, the mixtures were evaluated for molecular weight by gel permeation chromatography (GPC). The total monomer conversion (mole%) was determined from NMR analysis using the following calculation. The results are shown in Tables 11A and 11B.

A: amount of poly-2EHA-IBA plus unreacted monomer (2EHA and IBA)=(integral of resonances at 3.65 ppm to 4.09 ppm)

B: amount of unreacted monomer 2EHA and IBA (integral of resonance at 5.76 ppm) Total conversion=100*((A-(2*B))/A)

TABLE 11A

Compositions for 2EHA Polymer and IBA

| Example | Initial 2EHA Polymer Solution | Total Acrylate Conversion (mole %) |
|---|---|---|
| C4 | C2-8 | 87 |
| 7 | 4-8 | 90 |

C: Comparative Example

TABLE 11B

Results for 2EHA and IBA

Molecular Weights

| | Initial 2EHA Polymer | | | Final 2EHA/IBA Copolymer | | |
|---|---|---|---|---|---|---|
| Example | Mn (grams/mole) | Mw (grams/mole) | PDI | Mn (grams/mole) | Mw (grams/mole) | PDI |
| C4 | 50,100 | 111,900 | 2.23 | 45,100 | 94,300 | 2.09 |
| 7 | 33,400 | 59,400 | 1.78 | 76,200 | 145,900 | 1.91 |

C: Comparative Example

Examples 8-9 and Comparative Example 5

Copolymers of the 2EHA polymers Examples 1 (1-8), 3 (3-8), and C1 (C1-8), prepared as described above, and isobornyl acrylate (IBOA) were prepared as follows. In flasks, isobornyl acrylate (IBOA, 7.00 grams), and ethyl acetate (17.00 grams) were added to the final polymer solutions (34 grams) of Examples 1 (1-8), 3 (3-8), and C1 (C1-8). The solutions were purged with dry nitrogen for 10 minutes. The flasks were then held under a positive pressure of nitrogen, stirred magnetically, and irradiated with light emitting diodes (LED) using a 365 nanometer LED array (Model LED365-0556 LED Bank, Clearstone Technologies, Incorporated) at a power setting of 15% and a distance of 3 inches from the flask edge. The total energy provided after an exposure time of 5 minutes was 1850 milliJoules/square centimeters at the surface of the flask. After LED exposure, the solution was evaluated for molecular weight by gel permeation chromatography (GPC) and isobornyl acrylate conversion (NMR). IBOA conversion was calculated as the amount of poly(IBOA) (integral of resonance at 4.58 ppm divided by the sum of poly(IBOA) and unreacted monomer IBOA (integral of resonance at 4.71 ppm) multiplied by 100. The results are shown in Tables 12A and 12B.

TABLE 12A

Compositions for 2EHA Polymer and IBOA

| Example | Initial 2EHA Polymer Solution | Irradiation Time (minutes) | IBOA Conversion (mole %) |
|---|---|---|---|
| C5 | C1-8 | 55.0 | 70.1 |
| 8 | 1-8 | 49.5 | 71.2 |
| 9 | 3-8 | 51.5 | 68.6 |

C: Comparative Example

TABLE 12B

Results for 2EHA Polymer and IBOA

Molecular Weights

| | Initial 2EHA Polymer | | | Final 2EHA/IBA Copolymer | | |
|---|---|---|---|---|---|---|
| Example | Mn (grams/mole) | Mw (grams/mole) | PDI | Mn (grams/mole) | Mw (grams/mole) | PDI |
| C5 | 83,900 | 219,400 | 2.62 | 46,000 | 166,200 | 3.61 |
| 8 | 25,900 | 45,800 | 1.77 | 29,400 | 52,000 | 1.77 |
| 9 | 35,600 | 70,500 | 1.98 | 38,400 | 74,800 | 1.95 |

Comparative Example 6

Polymers of butyl acrylate were prepared using Photoinitiator 1 (PI-1) as follows. A solution was prepared containing 25.0 grams (195 millimoles) of butyl acrylate (BA) and 0.164 grams (0.85 millimoles) PI-1. Aliquots of approximately 1 gram of this solution were added to individual vials, purged with nitrogen for two minutes, and then sealed. The vials were irradiated with a UV lamp (OSRAM SYLVANIA F15T8/BLB Blacklight Blue, peak wavelength of 362 nanometers) placed 12.7 centimeters above the vials. The total energy provided to the vial from that distance after an exposure time of 8 minutes was 336 milliJoules/square centimeter. The vials were removed from the light at various time intervals and evaluated using NMR for monomer conversion, molecular weight, and fraction of free initiator.

One- and two-dimensional (2D) NMR experiments were run to assign the free initiator and polymer end groups. The methyl keto resonance of PI-1 was used to track the amount of free initiator. The assignments determined from 2D NMR analysis were 2.33 ppm for free initiator and 2.12 ppm for polymer chain end. Each resonance has a correlation distinctive for a ketone functionality in the gHMBC experiment at 201.4 and 207.0 ppm, respectively. Each resonance was divided by 3 (number of protons) to determine the molar amount of each species and quantitative values were calculated as described in the NMR Analysis test method above. The results are shown in Table 13.

TABLE 13

NMR Results for BA Polymer and PI-1

| Example | Irradiation time (minutes) | BA conversion (wt %) | Mn (grams/mole) | Fraction of free initiator (mole %) |
|---|---|---|---|---|
| C6-1 | 4 | 4 | 349,900 | 99 |
| C6-2 | 8 | 19 | 299,900 | 98 |
| C6-3 | 15 | 72 | 192,000 | 84 |
| C6-4 | 24 | 83 | 177,000 | 82 |

C: Comparative Example

Example 10

Polymers of butyl acrylate were prepared using Photoinitiator 4 (PI-4) as follows. The procedure of Comparative Example 6 was repeated with the following modifications. A solution containing 25.0 grams (195 millimoles) of BA and 0.200 grams (0.97 millimoles) PI-4 was used. One- and two-dimensional (2D) NMR experiments were run to assign the free initiator and polymer end groups. The methyl keto or sulfur-methine resonance of PI-4 was used to track the amount of free initiator and polymer chain ends. The assignments determined from 2D NMR analysis were 4.38 ppm for free initiator (S-CH) and 2.14 ppm for polymer chain end ($CH_3$ keto). The sulfur-methine resonance was divided by 1 (number of protons) to determine the molar amount of free initiator and the polymer bound keto $CH_3$ resonance was divided by 3 (number of protons) to determine the molar amount of polymer chains. Quantitative values were calculated as described in the NMR Analysis test method above. The results are shown in Table 14.

TABLE 14

NMR Results for BA Polymer and PI-4

| Example | Irradiation time (minutes) | BA conversion (wt %) | Mn (grams/mole) | Fraction of free initiator (mole %) |
|---|---|---|---|---|
| 10-1 | 5 | 24 | 12,700 | 47 |
| 10-2 | 7 | 50 | 16,500 | 15 |
| 10-3 | 12 | 76 | 20,300 | 3 |

Comparative Example 7

Polymers of butyl acrylate were prepared using Photoinitiator 2 (PI-2) as follows. The procedure of Comparative Example 6 was repeated with the following modifications. A solution containing 25.0 grams (195 millimoles) of BA and 0.212 grams (0.88 millimoles) PI-2 was used. One- and two-dimensional (2D) NMR experiments were run to assign the free initiator and polymer end groups. The aromatic resonance next to the keto group of PI-2 was used to track the amount of free initiator and polymer chain ends. The assignments determined from 2D NMR analysis were 8.04 ppm (doublet) for free initiator and 7.94 ppm (doublet) for polymer chain ends. Each resonance was divided by 2 (number of protons) to determine the molar amount of each species and quantitative values were calculated as described in the NMR Analysis test method above. The results are shown in Table 15.

TABLE 15

NMR Results for BA Polymer and PI-2

| Example | Irradiation time (minutes) | BA conversion (wt %) | Mn (grams/mole) | Fraction of free initiator (mole %) |
|---|---|---|---|---|
| C7-1 | 2 | 2 | 36,300 | 99 |
| C7-2 | 4 | 17 | 50,900 | 91 |
| C7-3 | 10 | 49 | 44,000 | 69 |
| C7-4 | 15 | 84 | 41,900 | 43 |
| C7-5 | 24 | 92 | 41,400 | 39 |

C: Comparative Example

FIG. 1 shows the aromatic region of the $^1$H NMR spectrum for Comparative Example 7 after 84% conversion of the monomer. Assignments of resonances used to quantify initiator related species are marked with an arrow.

Example 11

Polymers of butyl acrylate were prepared using Photoinitiator 7 (PI-7) as follows. The procedure of Comparative Example 7 was repeated with the following modifications. A solution containing 25.0 grams (195 millimoles) of BA and 0.196 grams (0.73 millimoles) PI-7 was used. One- and two-dimensional (2D) NMR experiments were run to assign the free initiator and polymer end groups. The aromatic resonance next to the keto group of PI-7 was used to track the amount of free initiator and polymer chain ends. The assignments determined from 2D NMR analysis were 8.03 ppm for free initiator (doublet) and 7.88-7.98 ppm (multiple doublets) for polymer chain ends. Each resonance was divided by 2 (number of protons) to determine the molar amount of each species and quantitative values were calculated as described in the NMR Analysis test method above. The results are shown in Table 16.

TABLE 16

NMR Results for BA Polymer and PI-7 (UV Blacklight Blue Lamp)

| Example | Irradiation time (minutes) | BA conversion (wt %) | Mn (grams/mole) | Fraction of free initiator (mole %) |
|---|---|---|---|---|
| 11-1 | 1.5 | 10 | 10,800 | 70 |
| 11-2 | 3.0 | 18 | 13,000 | 52 |
| 11-3 | 8.0 | 31 | 15,600 | 31 |
| 11-4 | 5.0 | 35 | 16,100 | 23 |
| 11-5 | 10.0 | 53 | 19,600 | 10 |
| 11-6 | 12.0 | 74 | 25,000 | 2 |
| 11-7 | 20.0 | 79 | 28,100 | 3 |

Figure 2:
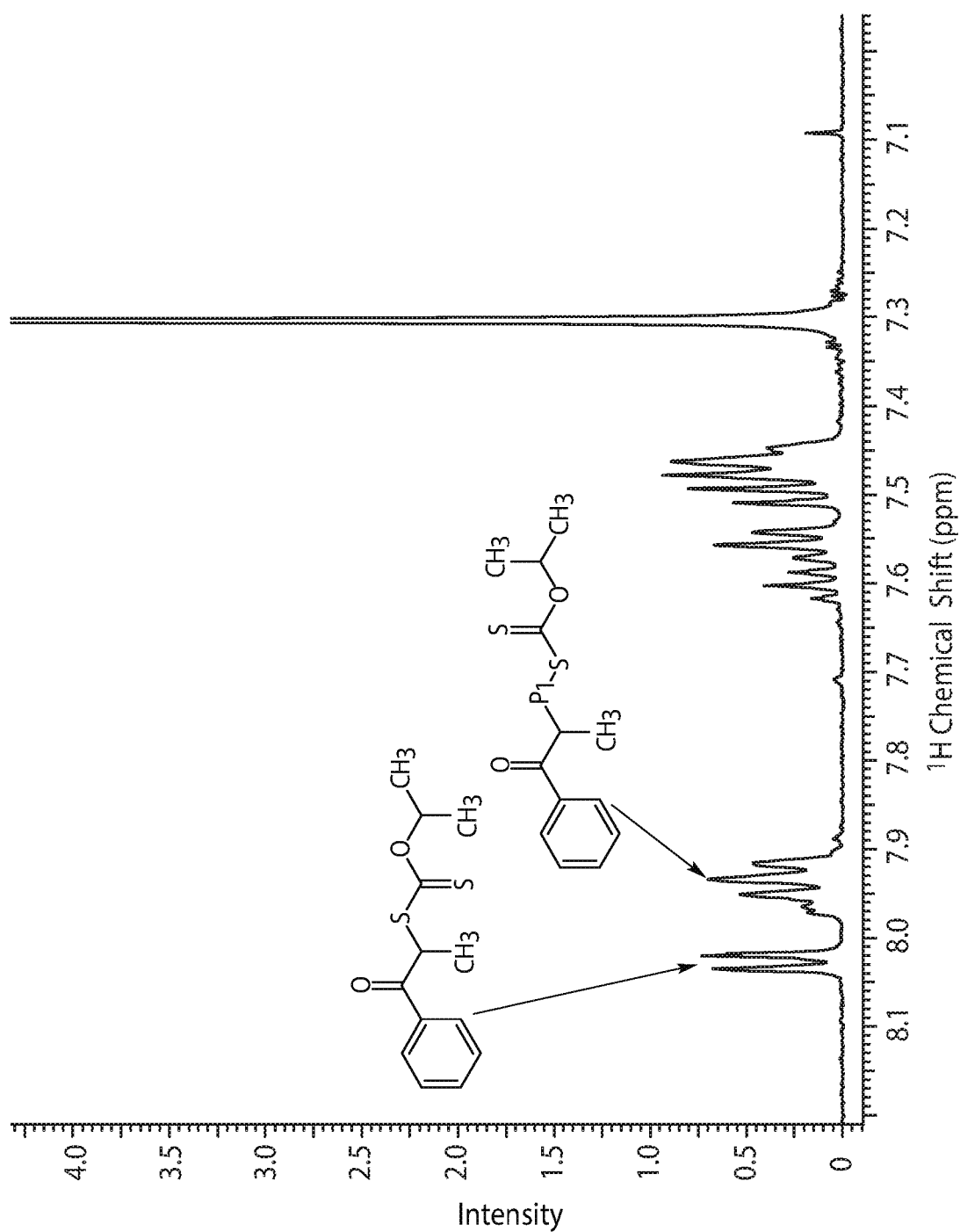
FIG. 2 shows the aromatic region of the $^1$H NMR spectrum for Example 10 after 31 percent conversion of the monomer.

FIG. 2 shows the aromatic region of the $^1$H NMR spectrum for Example 11 after 31% conversion of the monomer. Assignments of resonances used to quantify initiator related species are marked with an arrow.

Example 12

Example 11 was repeated using the same solution with the following modifications. The vials were irradiated with light emitting diodes (LED) using a 365 nanometer LED array (Model LED365-0556 LED Bank, Clearstone Technologies, Incorporated) at a power setting of 50% and a distance of 3 inches from the nearest vial edge. The total energy provided after an exposure time of ten seconds was 631 milliJoules/square centimeter at the surface of the solution. One- and two-dimensional (2D) NMR experiments were run to assign the free initiator and polymer end groups. The NMR spectral assignments were the same as for Example 10. The results are shown in Table 17.

TABLE 17

NMR Results for BA Polymer and PI-7 (UV LED Array)

| Example | Irradiation time (minutes) | BA conversion (wt %) | Mn (grams/mole) | Fraction of free initiator (mole %) |
|---|---|---|---|---|
| 12-1 | 0.5 | 26 | 13,700 | 37 |
| 12-2 | 1.0 | 51 | 19,400 | 11 |
| 12-3 | 1.5 | 69 | 24,700 | 5 |
| 12-4 | 2.0 | 80 | 28,700 | 2 |
| 12-5 | 2.5 | 86 | 30,300 | 0 |
| 12-6 | 3.0 | 90 | 32,000 | 0 |

Examples 10-12 and Comparative Examples 6-7 shows that initiators PI-4 and PI-7 initiate polymer chains more efficiently than PI-1 and PI-2.

Examples 13-15

Acrylic-based pressure sensitive adhesive tapes were prepared using PI-7 as follows. Compositions were prepared using the materials and amounts shown in Table 18. Isooctyl acrylate (IOA, 3M Corporation, St. Paul, Minn.), acrylic acid (AA, BASF Corporation, Florham Park, N.J.), and photoinitiator (PI-7) were combined. The mixtures were purged with nitrogen for 5 minutes then exposed to an OSRAM SYLVANIA F40/350BL BLACKLIGHT (peak wavelength of 352 nanometers, 40 Watts) at a distance of 10 centimeters from the lamp with mixing until a polymeric syrup having a Brookfield viscosity of 100 to 8000 centiPoise was formed. To the polymeric syrups thus obtained were added 2,2-dimethoxy-2-phenylacetophenone (OMNIRAD 651, IGM Resins, Saint Charles, Ill., USA), hexanediol diacrylate (HDDA), and in Example 14 a tackifying resin RR6108 (REGALREZ 6108, Eastman Chemical, Kingsport, Tenn.). These were mixed for one hour to give pre-adhesive syrup compositions. These compositions were then knife coated between a polyester release liner and the primed surface of 0.002 inch (127 micrometers) thick, primed poly(ethylene terephthalate) film (HOSTAPHAN 3SAB PET film, Mitsubishi Polyester Film, Greer, S.C.) at a thickness of 0.002 inches (127 micrometers). The coated compositions were irradiated for five minutes using UVA lamps (OSRAM SYLVANIA F40/350BL BLACKLIGHT, peak wavelength of 352 nanometers, 40 Watts) to provide total UVA energy of 2100 milliJoules/square centimeter. The resulting pressure sensitive adhesive tapes were evaluated for 180 degree angle peel adhesion strength and shear strength as described in the test methods. The results are shown in Table 18.

TABLE 18

Compositions, Peel, and Shear Results

| Example | IOA (grams) | AA (grams) | PI-7 (grams) | RR6108 (grams) | 1651 (grams) | HDDA (grams) | Peel Adhesion (SS) oz/in (N/dm) | 70° C. Shear (minutes) |
|---|---|---|---|---|---|---|---|---|
| 13 | 9.00 | 1.00 | 0.001 | — | 0.015 | 0.010 | 74.2 (82.5) | 10,000+ |
| 14 | 9.50 | 0.50 | 0.001 | — | 0.015 | 0.010 | 37.9 (41.5) | 10,000+ |
| 15 | 9.80 | 0.20 | 0.001 | 1.00 | 0.015 | 0.010 | 21.7 (23.7) | 10,000+ |

What is claimed is:

1. A polymeric material of Formula (II)

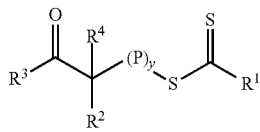

(II)

wherein $R^1$ is an alkoxy, aralkyloxy, alkenoxy or —$N(R^5)_2$;

$R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group;

$R^4$ is an alkyl or hydrogen;

each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated and optionally fused to one or more second rings that are carbocyclic or heterocyclic;

each $R^6$ is an alkylene;

$R^7$ is an alkyl;

n is an integer greater than or equal to zero;

each P is a polymeric block that comprises a polymerized product of a first monomer composition comprising at least one monomer having a single ethylenically unsaturated group; and y is an integer in a range of 1 to 10.

2. The polymeric material of claim 1, wherein the polymeric material of Formula (II) is of Formula (II-A)

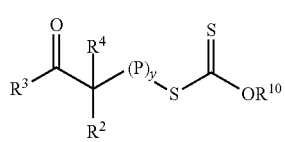

(II-A)

wherein —$OR^{10}$ is alkoxy, aralkyloxy, or alkenoxy.

3. The polymeric material of claim 1, wherein the polymeric material of Formula (II) is of Formula (II-B)

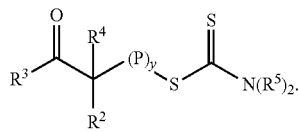

(II-B)

4. The polymeric material of claim 1, wherein $R^1$ is alkoxy or of formula —$N(R^5)_2$, where each $R^5$ is an alkyl.

5. The polymeric material of claim 1, wherein $R^4$ is hydrogen.

6. The polymeric material of claim 1, wherein $R^2$ is alkyl.

7. The polymeric material of claim 1, wherein y is equal to 1, 2, or 3.

8. A crosslinkable composition comprising:

a) a polymeric material of Formula (II)

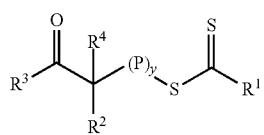

(II)

wherein $R^1$ is an alkoxy, aralkyloxy, alkenoxy or —$N(R^5)_2$;

$R^2$ and $R^3$ are each independently an alkyl, aryl, aralkyl, alkaryl, or a group of formula —$R^6$—$(OR^6)_n$—$OR^7$, or $R^2$ and $R^3$ combine to form a ring structure containing the carbonyl group;

$R^4$ is an alkyl or hydrogen;

each $R^5$ is an alkyl, aryl, or two adjacent $R^5$ groups combine with the nitrogen, to which they are both attached, to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic;

each $R^6$ is an alkylene;

$R^7$ is an alkyl;

n is an integer greater than or equal to zero;

each P is a polymeric block that comprises a polymerized product of a first monomer composition comprising at least one monomer having a single ethylenically unsaturated group;

y is an integer in a range of 1 to 10; and b) a second monomer composition comprising a crosslinking monomer having at least two ethylenically unsaturated groups.

9. The crosslinkable composition of claim 8, wherein the polymeric material is an elastomeric material and wherein the crosslinkable composition optionally further comprises a tackifier.

10. The crosslinkable composition of claim 8, wherein $R^4$ is hydrogen.

11. The crosslinkable composition of claim 8, wherein $R^2$ is alkyl.

12. The crosslinkable composition of claim 8, wherein $R^1$ is alkoxy or $-N(R^5)_2$, where $R^5$ is alkyl.

13. The crosslinkable composition of claim 8, wherein y is equal to 1, 2, or 3.

14. A crosslinked composition comprising a cured product of the crosslinkable composition of claim 8.

15. An article comprising a first substrate and a crosslinked composition positioned adjacent to the first substrate, wherein the crosslinked composition is of claim 14.

* * * * *

UNITED STATES PATENT AND TRADEMARK OFFICE
CERTIFICATE OF CORRECTION

PATENT NO. : 10,941,234 B2
APPLICATION NO. : 15/733412
DATED : March 9, 2021
INVENTOR(S) : Lewandowski et al.

It is certified that error appears in the above-identified patent and that said Letters Patent is hereby corrected as shown below:

On the Title Page

Page 2, Column 2
Other Publications, Line 37, Delete "a-sulfenylation" and insert -- α-sulfenylation --, therefor.

In the Specification

Column 1
Line 5, Delete "APPLICATION" and insert -- APPLICATIONS --, therefor.
Line 42, Delete "atom transfer polymerization (ATRP)" and insert -- atom transfer radical polymerization (ATRP) --, therefor.

Column 4
Line 39, After "thereof" insert -- . --.
Line 43, Begin new paragraph with "The term "aralkyl" ...".
Line 65, Begin new paragraph with "The term "heterocyclic ring" ...".

Column 5
Line 11, Delete "$CH_2=CHR^c(CO)$—" and insert -- $CH_2=CHR^c$—(CO)— --, therefor.
Line 40, Delete "—$N(R^5)2$." and insert -- —$N(R^5)_2$. --, therefor.
Line 53, Delete "Formulas" and insert -- Formula --, therefor.

Column 7
Line 7, Delete "thiomorpholino," and insert -- thiomorpholine, --, therefor.
Line 9, Begin new paragraph with "Groups $R^2$...".

Column 8
Line 8, Delete "R'" and insert -- $R^1$ --, therefor.
Line 12, Delete "tetralkyl" and insert -- tetraalkyl --, therefor.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

Column 13
Line 12, Delete "P²or" and insert -- $P^2$, or --, therefor.

Column 22
Line 57, After "thereof" insert -- . --.

Column 23
Line 57, Delete "3,3,5 trimethylcyclohexyl" and insert -- 3,3,5-trimethylcyclohexyl --, therefor.
Line 59, After "thereof" insert -- . --.

Column 24
Line 18, After "thereof" insert -- . --.

Column 27
Line 51, After "thereof" insert -- . --.

Column 29
Line 67, Delete "CS" and insert -- C5 --, therefor.

Column 31
Line 58, Delete "Formula (I)" and insert the same on Column 31, Line 57 as a continuation of the same paragraph.

Column 33
Line 59, After "Group" insert -- $R^4$ --.

Column 34
Line 39, Delete "—N(R⁵)2." and insert -- —$N(R^5)_2$. --, therefor.

Column 36
Line 1, Delete "In Formula (I), group R¹, R², and R³ are the same as in Formula (II)." and insert the same on Column 35, Line 66 as a continuation of the same paragraph.
Line 49, Delete "embodiment" and insert -- embodiments --, therefor.

Column 38
Line 41, Delete "angle)(15°)" and insert -- angle (15°) --, therefor.
Line 50, Before "NMR" insert -- $^1H$ --.

Column 40
Line 1, Delete "Carboonodithioic" and insert -- Carbonodithioic --, therefor.

Column 41
Line 7, Delete "PI-6)" and insert -- (PI-6) --, therefor.

Column 42
Line 1, After "acid" insert -- O-isopropyl --.

Column 47
Line 19, Delete "2EHA/IBA" and insert -- 2EHA/IBOA --, therefor.